United States Patent
Takasugi

(10) Patent No.: US 9,775,494 B2
(45) Date of Patent: Oct. 3, 2017

(54) OBLIQUE-VIEWING OBJECTIVE OPTICAL SYSTEM AND ENDOSCOPE FOR OBLIQUE VIEWING USING THE SAME

(71) Applicant: OLYMPUS CORPORATION, Hachioji-shi, Tokyo (JP)

(72) Inventor: Yoshiharu Takasugi, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/342,352

(22) Filed: Nov. 3, 2016

(65) Prior Publication Data

US 2017/0049305 A1    Feb. 23, 2017

Related U.S. Application Data

(63) Continuation of application No. PCT/JP2015/082288, filed on Nov. 17, 2015.

(30) Foreign Application Priority Data

Feb. 20, 2015 (JP) ................................ 2015-031361

(51) Int. Cl.
*G02B 23/00* (2006.01)
*A61B 1/00* (2006.01)
(Continued)

(52) U.S. Cl.
CPC ...... *A61B 1/00179* (2013.01); *A61B 1/00096* (2013.01); *A61B 1/00177* (2013.01);
(Continued)

(58) Field of Classification Search
CPC ... G02B 9/00; G02B 9/34; G02B 9/58; G02B 13/00; G02B 13/0015; G02B 13/004; G02B 23/00; G02B 23/02; G02B 23/24; G02B 23/2415; G02B 23/243; A61B 1/00096; A61B 1/00179; A61B 1/00188
See application file for complete search history.

(56) References Cited

U.S. PATENT DOCUMENTS

| 4,037,938 A | 7/1977 | Yamashita et al. |
| 7,821,720 B2* | 10/2010 | Wang .................. G02B 23/243 359/656 |
| 8,441,529 B2* | 5/2013 | Sasamoto .......... A61B 1/00188 348/65 |

FOREIGN PATENT DOCUMENTS

| JP | 51062053 A | 5/1976 |
| JP | 05288985 A | 11/1993 |

(Continued)

OTHER PUBLICATIONS

International Search Report (ISR) and Written Opinion dated Jan. 12, 2016 issued in International Application No. PCT/JP2015/082288.

*Primary Examiner* — Thong Nguyen
(74) *Attorney, Agent, or Firm* — Holtz, Holtz & Volek PC

(57) ABSTRACT

An oblique-viewing objective optical system includes in order from an object side, a front-side lens group which includes a negative lens, an optical path converting element, an aperture stop, and a rear-side lens group having a positive refractive power, wherein the rear-side lens group includes a positive lens and a cemented lens having a positive refractive power, and the cemented lens includes in order from the object side a positive lens and a negative lens.

2 Claims, 22 Drawing Sheets

(51) Int. Cl.
    *G02B 23/24*     (2006.01)
    *G02B 13/04*     (2006.01)
    *G02B 23/26*     (2006.01)
    *G02B 23/02*     (2006.01)

(52) U.S. Cl.
    CPC .......... *A61B 1/00186* (2013.01); *G02B 13/04* (2013.01); *G02B 23/02* (2013.01); *G02B 23/24* (2013.01); *G02B 23/243* (2013.01); *G02B 23/26* (2013.01)

(56) References Cited

FOREIGN PATENT DOCUMENTS

| | | | |
|---|---|---|---|
| JP | 08179226 | A | 7/1996 |
| JP | 3385090 | B2 | 3/2003 |
| JP | 3574484 | B2 | 10/2004 |
| JP | 4439184 | B2 | 3/2010 |
| JP | 4814746 | B2 | 11/2011 |

\* cited by examiner

OBLIQUE-VIEWING OBJECTIVE OPTICAL SYSTEM AND ENDOSCOPE FOR OBLIQUE VIEWING USING THE SAME

CROSS-REFERENCE TO RELATED APPLICATION

The present application is a continuation application of PCT/JP2015/082288 filed on Nov. 17, 2015 which is based upon and claims the benefit of priority from Japanese Patent Application No. 2015-031361 filed on Feb. 20, 2015; the entire contents of which are incorporated herein by reference.

BACKGROUND OF THE INVENTION

Field of the Invention

The present invention relates to an oblique-viewing objective optical system which is provided with an optical path converting element, and an endoscope for oblique viewing using the same.

Description of the Related Art

In recent years, in image pickup elements such as a CCD (Charged Coupled Devices) and a C-MOS (Complementary Metal Oxide Semiconductor), due to the progress in microfabrication technology, refining of pixels and small-sizing of an element have been advancing. Especially, recently, image pickup elements having extremely fine pixels such as an image pickup element with a pixel pitch of approximately 2 μm to 3 μm have been manufactured. Thus, the image pickup elements in recent years have a large number of pixels and a small size as compared to former image pickup elements.

Moreover, when a lens outer-diameter and an overall length of an optical system are made small-sized, it becomes difficult to make a light ray emerged from the optical system be incident perpendicularly on a light-receiving surface of an image pickup element. In this case, the light ray is incident obliquely (hereinafter, referred to as 'oblique incidence') on the light-receiving surface. Therefore, image pickup elements such as a CCD and a C-MOS of recent years have been designed on the premise that an optimum incidence of a light ray on the light-receiving surface is oblique incidence. In such manner, the image pickup elements in recent years have an oblique-incidence characteristic.

By using the image pickup element with a large number of pixels and small-size in an endoscope, it is possible to achieve a high-quality image and thinning of an endoscope diameter. With this, an objective optical system having a high performance and small-size has been sought for an objective optical system for endoscope. An optical system with a high performance is an optical system with a high resolving power, and in which an aberration is corrected favorably.

As an objective optical system for endoscope, an oblique-viewing objective optical system is available. In the oblique viewing objective optical system, a front viewing, a side viewing, and a rear viewing are carried out.

FIG. 1 is an example of a conventional oblique-viewing objective optical system. An oblique-viewing optical system 1 is an oblique-viewing optical system that carries out the side viewing. The oblique-viewing objective optical system 1 includes a front-side lens group 2, a prism 3, and a rear-side lens group 4. In the oblique-viewing objective optical system 1, due to the prism 3, an optical axis of the front-side lens group 2 and an optical axis of the rear-side lens group 4 are orthogonal.

FIG. 2 is another example of the conventional oblique-viewing objective optical system. An oblique-viewing optical system 5 is an oblique-viewing optical system that carries out the front viewing. An oblique-viewing objective optical system 5 includes a front-side lens group 6, a prism 7, and a rear-side lens group 8. In the oblique-viewing objective optical system 5, due to the prism 7, an optical axis of the front-side lens group 6 and an optical axis of the rear-side lens group intersect (but are not orthogonal).

As shown in FIG. 1 and FIG. 2, in the oblique-viewing objective optical system, an optical path converting element with a large path length in glass is disposed in the optical system. Therefore, especially in the oblique-viewing objective optical system, a large space for disposing an optical path converting element such as a prism is necessary. Consequently, in the oblique-viewing objective optical system, an overall length of the optical system becomes long as compared to a direct-viewing objective optical system. Thus, since an oblique-viewing objective optical system tends to be large-sized as compared to a direct-viewing objective optical system, further small-sizing has been sought in the oblique-viewing objective optical system. Oblique-viewing objective optical systems have been disclosed in Japanese Patent Application Laid-open Publication No. Sho 51-62053, Japanese Patent Publication Nos. 3385090, 3574484, 4439184, and 4814746.

An oblique-viewing objective optical system disclosed in Japanese Patent Application Laid-open Publication No. Sho 51-62053 includes a front-group diverging lens system and a rear-group converging lens system. This objective optical system is an optical system that is supposed to be used in an image fiber. Therefore, in this oblique-viewing objective optical system, an arrangement has been made such that a light ray emerged from the oblique-viewing objective optical system can be incident almost perpendicularly with respect to an end-surface of incidence of fiber.

An oblique-viewing objective optical system disclosed in Japanese Patent Publication No. 3385090 includes a first lens group including one negative lens and a second lens group having a positive refractive power. In this oblique-viewing objective optical system, for correcting a chromatic aberration, a glass material with small dispersion (glass material with a large Abbe number) has been used for the negative in the first lens group lens and a prism.

An oblique-viewing objective optical system disclosed in Japanese Patent Publication No. 3574484 includes a front group having a negative focal length and a rear group having a positive focal length.

An oblique-viewing objective optical system disclosed in Japanese Patent Publication No. 4439184 includes a first lens group including a single lens having a negative refractive power, a second lens group having a positive refractive power, and a third lens group having a positive refractive power. In this oblique-viewing objective optical system, the third lens group includes in order from an object side, a cemented lens of a negative lens and a positive lens. By making such arrangement, telecentricity is secured. In other words, in the oblique-viewing objective optical system disclosed in patent literature 4, an arrangement is made such that a light ray emerged from the oblique-viewing objective optical system is incident almost perpendicularly with respect to a light-receiving surface of a CCD.

An oblique-viewing objective optical system disclosed in Japanese Patent Publication No. 4814746 includes a first group having a negative refractive power and a second group having a positive refractive power.

Incidentally, in an oblique-viewing objective optical system and a direct-viewing objective optical system, the optical system has been held by a frame member. At a time of assembling, the optical system is to be installed by jigs and tools for assembling via the frame member. Moreover, the optical system after assembly is installed on a front-end portion of the endoscope via the frame member. Therefore, it is necessary to secure a length of certain degree for a fitting portion of the frame member.

FIG. 3 is an example of the frame member of the oblique-viewing objective optical system. An oblique-viewing objective optical system 9 is an oblique-viewing objective optical system that carries out side viewing. The oblique-viewing objective optical system 9 includes a front-side lens group 10, a prism 11, and a rear-side lens group 12. In the oblique-viewing objective optical system 9, by reflecting once at the prism 11, an optical axis of the front-side lens group 10 and an optical axis of the rear-side lens group 12 become orthogonal.

In the oblique-viewing objective optical system 9, the front-side lens group 10 and the prism 11 are held by a frame member 13, and the rear-side lens group 12 is held by a frame member 14. Moreover, an image pickup element 15 is held by a frame member 16.

FIG. 4 and FIG. 5 are other examples of a frame member of an oblique-viewing objective optical system. An oblique-viewing objective optical system 17 and an oblique-viewing objective optical system 18 are oblique-viewing objective optical systems that carry out front viewing. In the oblique-viewing objective optical system 17 and the oblique-viewing objective optical system 18, by reflecting twice at a prism, an optical axis of a front-side lens group and an optical axis of a rear-side lens group intersect. Two frame members have been used in the oblique-viewing objective optical system 17 and three frame members have been used in the oblique-viewing objective optical system 18.

SUMMARY OF THE INVENTION

An oblique-viewing objective optical system according to the present invention comprises in order from an object side, a front-side lens group which includes a negative lens, an optical path converting element, an aperture stop, and a rear-side lens group having a positive refractive power, wherein the rear-side lens group includes a positive lens and a cemented lens having a positive refractive power, and the cemented lens includes in order from the object side, a positive lens and a negative lens, and the following conditional expressions (1), (2), (3), (4), and (5) are satisfied:

$$-2.0 < f_F/f < -1.3 \quad (1),$$

$$1.7 < f_R/f < 2.7 \quad (2),$$

$$0.63 < |f_F/f_R| < 0.88 \quad (3),$$

$$2.4 < D1/f < 4.4 \quad (4), \text{ and}$$

$$1.1 < D2/f < 1.7 \quad (5).$$

where, $f_F$ denotes a focal length of the front-side lens group, $f_R$ denotes a focal length of the rear-side lens group, $f$ denotes a focal length of the overall oblique-viewing objective optical system, D1 denotes an air-conversion length from an image-side surface of the negative lens in the front-side lens group up to the aperture stop, and D2 denotes an air-conversion length from an image-side surface of the rearmost lens in the rear-side lens group up to the image plane.

Moreover, an endoscope for oblique viewing according to the present invention comprises the oblique-viewing objective optical system.

DETAILED DESCRIPTION OF THE INVENTION

Figure 1:
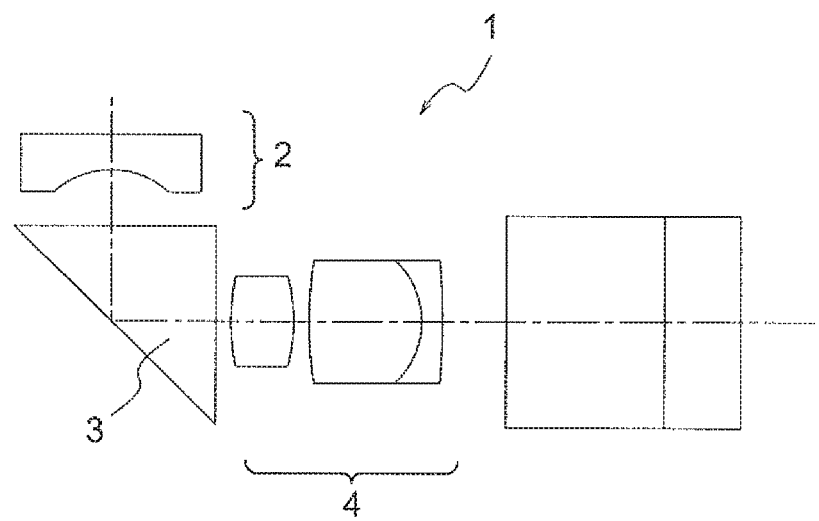
FIG. 1 is a diagram showing a conventional oblique-viewing objective optical system.
Figure 2:
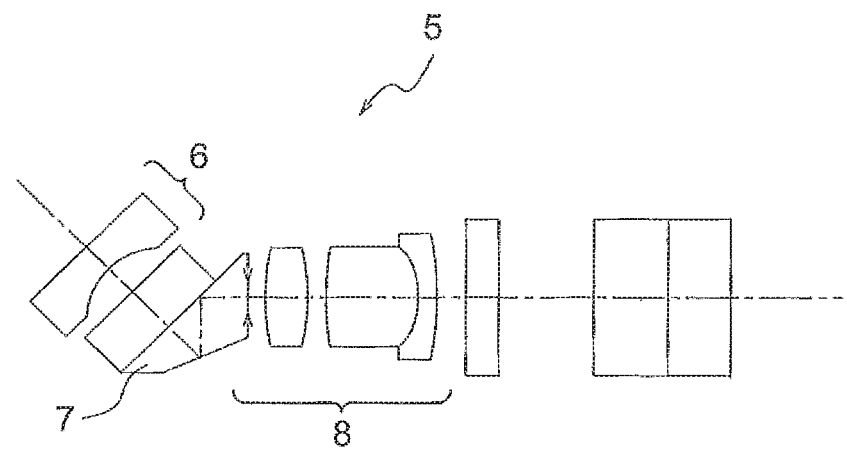
FIG. 2 is a diagram showing another conventional oblique-viewing objective optical system.
Figure 3:
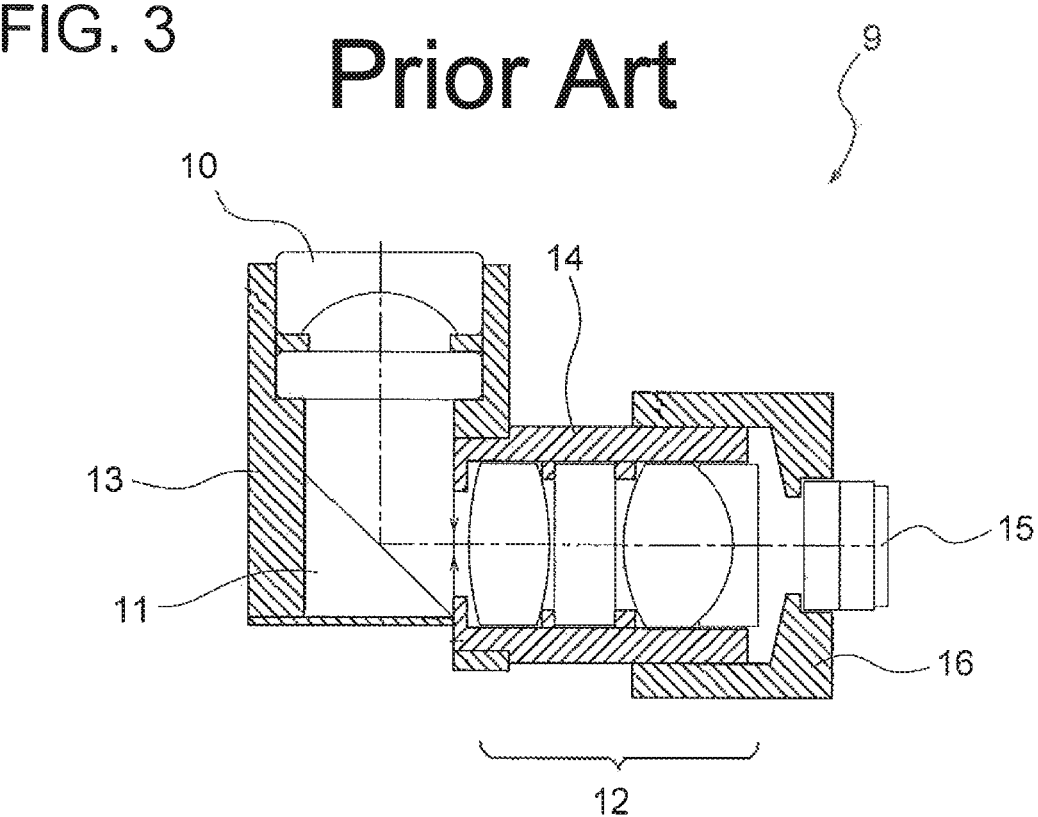
FIG. 3 is a diagram showing a frame member of an oblique-viewing objective optical system.
Figure 4:
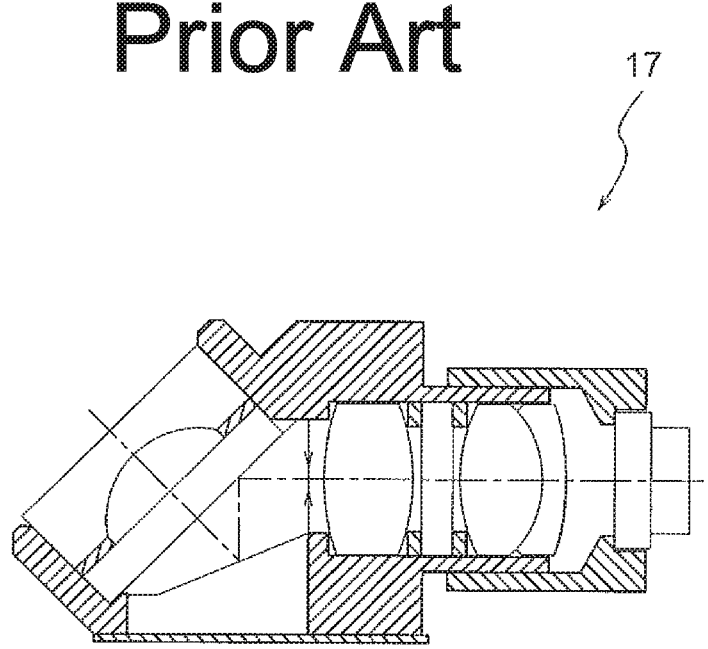
FIG. 4 is a diagram showing another frame member of an oblique-viewing objective optical system.
Figure 5:
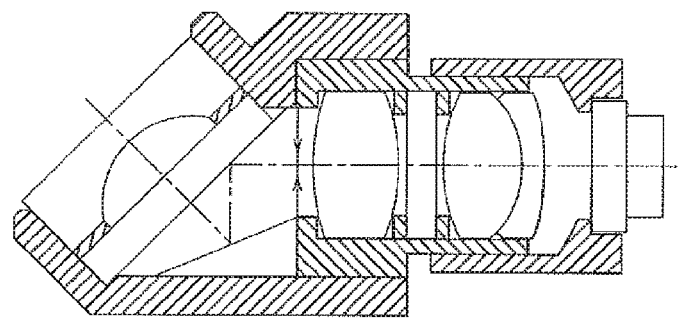
FIG. 5 is a diagram showing still another frame member of an oblique-viewing objective optical system.

Reasons for adopting such arrangements and effects thereof in an oblique-viewing objective optical system according to the present embodiment will be described below by referring to the accompanying diagrams. However, the present invention is not limited to the oblique-viewing objective optical system according to the embodiment described below.

The oblique-viewing objective optical system according to the present embodiment includes in order from an object side, a front-side lens group which includes a negative lens, an optical path converting element, an aperture stop, and a rear-side lens group having a positive refractive power, and the rear-side lens group includes a positive lens and a cemented lens having a positive refractive power, and the cemented lens includes in order from the object side, a positive lens and a negative lens.

By disposing the optical path converting element near the aperture stop, or in other words, on the object side of the aperture stop or on the image side of the aperture stop, it is possible to suppress a height of a light ray at the optical path converting element to be low. As a result, it is possible to make a size of the optical path converting element small.

However, when the optical path converting element is disposed on the image side of the aperture stop, a distance from the aperture stop up to an image plane becomes long at least by an amount of a path length in glass of the optical path converting element. As this distance becomes long, a light ray emerging from the oblique-viewing objective optical system becomes almost perpendicular with respect to a light-receiving surface of an image pickup element. Consequently, an angle of the light ray emerging from the oblique-viewing objective optical system does not satisfy an oblique incidence characteristic of the image pickup element. As a result, there is an unevenness of brightness and unevenness in color in a peripheral portion of image.

Moreover, in assembling of the oblique-viewing objective optical system, focus adjustment is to be carried out. Therefore, when an attempt is made to forcedly satisfy the oblique incidence characteristic of the image pickup element, a distance necessary for the focus adjustment is inadequate. Moreover, since a light ray is to be bent forcedly according to the oblique incidence characteristic, an aberration occurs. As a result, the optical performance is degraded remarkably.

Therefore, in the oblique-viewing objective optical system according to the present embodiment, the optical path converting element is disposed on the object side of the aperture stop. Accordingly, since it is possible to shorten the distance from the aperture stop up to the image plane, the angle of a light ray emerging from the oblique-viewing objective optical system can be let to be an angle that satisfies the oblique incidence characteristic of the image pickup element comparatively easily.

Furthermore, the path length in glass becomes long on the object side of the aperture stop. Therefore, it is possible to secure appropriately a length of a frame member that holds the front-side lens group. As a result, it is possible to carry out with ease and accuracy the assembling of the oblique-viewing objective optical system and installation of the oblique-viewing objective optical system on a front-end portion of endoscope.

It is desirable that the cemented lens includes in order from the object side the positive lens and the negative lens. By making such arrangement, it is possible to make the oblique-viewing objective optical system small-sized. Moreover, it is possible to let the angle of a light ray emerging from the oblique-viewing objective optical system to be an angle that satisfies oblique incidence characteristic of the image pickup element.

When the cemented lens includes in order from the object side the negative lens and the positive lens, since a height of a light ray at the cemented lens becomes high, an outer diameter of lenses becomes large. Consequently, a workability of the lens is degraded. Moreover, an outer diameter of the oblique-viewing objective optical system as a whole also becomes large.

Furthermore, since a light ray is bent by an effect of the positive lens disposed on the image side, a light ray emerged from the oblique-viewing objective optical system becomes almost perpendicular with respect the light-receiving surface of the image pickup element. As a result, it is difficult to make an angle of the light ray emerging from the oblique-viewing objective optical system to be an angle that satisfies the oblique incidence characteristic of the image pickup element. When an attempt is made to satisfy the oblique incidence characteristic forcedly, since the light ray is bent substantially at a cemented lens surface, an aberration occurs. Consequently, an optical performance is degraded.

The oblique-viewing objective optical system according to the present embodiment has the abovementioned arrangement and the following conditional expressions (1) and (2) are satisfied:

$$-2.0 < f_F/f < -1.3 \quad (1),\text{ and}$$

$$1.7 < f_R/f < 2.7 \quad (2),$$

where, $f_F$ denotes a focal length of the front-side lens group,
$f_R$ denotes a focal length of the rear-side lens group, and
f denotes a focal length of the overall oblique-viewing objective optical system.

Conditional expression (1) regulates the focal length of the front-side lens group.

When falling below a lower limit value of conditional expression (1), since the refractive power of the front-side lens group becomes small, an angle of view of the oblique-viewing objective optical system becomes small. When an attempt is made to secure a large angle of view in this state, a distance from the negative lens in the front-side lens group (hereinafter, referred to as the 'front-side negative lens') up to the aperture stop becomes long. As the distance becomes long, since the height of a light ray between the front-side negative lens and the aperture stop becomes high, the front-side negative lens becomes large-sized, and the overall optical system becomes large-sized.

When exceeding an upper limit value of conditional expression (1), since the refractive power of the front-side lens group becomes large, the angle of view of the oblique-viewing objective optical system becomes large. As the angle of view becomes large, since the height of a light ray passing through the lens becomes high, an outer diameter of the lens becomes large. Furthermore, by the angle of view becoming large, a peripheral portion of an image observed becomes dark. For making the peripheral portion of image bright, illumination light has to be made further brighter. However, when the illumination light is made further brighter, it leads to making an illumination optical system large-sized. Both are not preferable for thinning of diameter of endoscope.

Furthermore, as the refractive power of the front-side lens group becomes large, since a radius of curvature of the front-side negative lens becomes small, processing of the lens becomes difficult. Furthermore, by the refractive power of the front-side negative lens becoming large, the degradation of optical performance is substantial especially when there is a decentering of lens. As a result, it becomes difficult to realize an oblique-viewing objective optical system having a stable optical performance.

Conditional expression (2) regulates the focal length of the rear-side lens group.

When falling below a lower limit value of conditional expression (2), since the refractive power of the rear-side lens group becomes large, an image position comes excessively close to the rear-side lens group. As the image position comes excessively close to the rear-side lens group, since a distance necessary for the focus adjustment becomes narrow, the distance necessary for the focus adjustment is inadequate. Consequently, a depth of a far-point side becomes shallower than a depth required originally.

Furthermore, as the refractive power of the rear-side lens group becomes large, a refractive power of each lens in the rear-side lens group also becomes large. In this case, since a radius of curvature of each lens becomes small, processing of lens becomes difficult.

When exceeding an upper limit value of conditional expression (2), since the refractive power of the rear-side lens group becomes large, the image position is separated apart excessively from the rear-side lens group. In this case, since the path length in glass from the aperture stop up to the image position becomes long, the overall optical system becomes large-sized.

By satisfying conditional expression (1) and conditional expression (2), in the oblique-viewing objective optical system according to the present embodiment, it is possible to optimize a balance of the refractive power of the front-side lens group and the refractive power of the rear-side lens group. As a result, it is possible to realize an oblique-viewing objective optical system in which various aberrations are corrected favorably.

It is preferable that the following conditional expression (1') is satisfied instead of conditional expression (1).

$$-1.9 < f_F/f < -1.4 \quad (1')$$

It is preferable that the following conditional expression (2') is satisfied instead of conditional expression (2).

$$1.8 < f_R/f < 2.5 \quad (2')$$

Furthermore, in the oblique-viewing objective optical system according to the present embodiment, it is preferable that the following conditional expression (3) is satisfied:

$$0.63 < |f_F/f_R| < 0.88 \quad (3),$$

where, $f_F$ denotes the focal length of the front-side lens group, and
$f_R$ denotes the focal length of the rear-side lens group.

Conditional expression (3) regulates a ratio of the focal length of the front-side lens group and the focal length of the rear-side lens group. By satisfying conditional expression (3), it is possible to optimize the balance of the refractive power of the front-side lens group and the refractive power of the rear-side lens group. As a result, it is possible to realize an oblique-viewing objective optical system in which various aberrations are corrected favorably.

When falling below a lower limit value of conditional expression (3), the focal length of the front-side lens group becomes short (the refractive power of the front-side lens group becomes large). Consequently, an angle of view of the oblique-viewing objective optical system becomes large. As the angle of view becomes large, since the height of a light ray passing through lens becomes high, an outer diameter of lens becomes large. Furthermore, by the angle of view becoming large, a peripheral portion of an image observed becomes dark. For making the peripheral portion of image bright, illumination light has to be made further brighter. However, when the illumination light is made further brighter, it leads to making an illumination optical system large-sized. Both are not preferable for thinning of diameter of endoscope.

Furthermore, the refractive power of the front-side negative lens becomes larger than the positive refractive power of the rear-side lens group. Consequently, an aberration that has an effect of the negative refractive power cannot be corrected adequately in the rear-side lens group. As a result, a curvature of field occurs in a positive direction.

Furthermore, the balance of the refractive power of the front-side lens group and the refractive power of the rear-side lens group becomes is disrupted. In this case, since an amount of astigmatism that occurs becomes large, particularly, an image plane in a meridional direction is inclined substantially in the positive direction. Consequently, when the lens is decentered, a decentration aberration is susceptible to occur in the image. Particularly, at the time of near-point observation, there is a possibility that a peripheral portion of image is blurred remarkably.

When exceeding an upper limit value of conditional expression (3), the focal length of the front-side lens group becomes long (the refractive power of the front-side lens group becomes small). Consequently, the angle of view of the oblique-viewing objective optical system becomes small.

Furthermore, the refractive power of the front-side negative lens becomes smaller than the positive refractive power of the rear-side lens group. Consequently, correction by the rear-side lens group becomes excessive with respect an aberration that has an effect of the negative refractive power. As a result, a substantial curvature of field occurs in the negative direction.

Moreover, the balance of the refractive power of the front-side lens group and the refractive power of the rear-side lens group becomes is disrupted. In this case, since the amount of astigmatism that occurs becomes large, the image plane in the meridional direction is inclined substantially in the negative direction. Consequently, when the lens is decentered, a decentration aberration is susceptible to occur in the image. Particularly, at the time of near-point observation, there is a possibility that a peripheral portion of image is blurred remarkably.

Moreover, in the oblique-viewing objective optical system according to the present embodiment, it is preferable that the following conditional expressions (4) and (5) are satisfied:

$$2.4 < D1/f < 4.4 \quad (4), \text{ and}$$

$$1.1 < D2/f < 1.7 \quad (5),$$

where,

D1 denotes an air-conversion length from an image-side surface of the negative lens in the front-side lens group up to the aperture stop, D2 denotes an air-conversion length from an image-side surface of the rearmost lens in the rear-side lens group up to the image plane, and f denotes the focal length of the overall oblique-viewing objective optical system.

Conditional expression (4) regulates the air-conversion length from the image-side surface of the negative lens in the front-side lens group up to the aperture stop. For instance, in an example 1 that will be described later, D1 is to be calculated by the following formula.

$$D1 = d2 + d3/n3 + d4 + d5/n5$$

When falling below a lower limit value of conditional expression (4), it becomes difficult to secure adequately a space for disposing the optical path converting element having an optimum shape of outer diameter. Consequently, shading of a light ray occurs in the optical path converting element. Moreover, by a light ray being incident at a position other than an optical surface of the optical path converting element, there is a possibility of a flare occurring in the image.

Moreover, it becomes difficult to secure appropriately a length of a frame member which holds the front-side lens group. In this case, the frame member cannot be held stably by jigs and tools for assembling. Consequently, it becomes difficult to carry out assembling and focus adjustment of the oblique-viewing objective optical system with high precision. Furthermore, it becomes difficult to install and fix the oblique-viewing objective optical system to the front-end portion of endoscope with high precision.

When exceeding an upper limit value of conditional expression (4), although it is possible to secure adequately the space for disposing the optical path converting element, the path length in glass from the front-side negative lens up to the aperture stop becomes excessively long. In this case, since the height of a light ray at the front-side negative lens becomes high, an outer diameter of the front-side negative lens becomes large. With this, the oblique-viewing objective optical system becomes large-sized. Furthermore, with the oblique-viewing objective optical system becoming large-sized, an outer diameter of an endoscope on which it is to be mounted also becomes large.

Conditional expression (5) regulates the air-conversion length from an image-side surface of the rearmost lens in the rear-side lens group up to the image plane. Here, the rearmost lens refers to a lens having a refractive power. Therefore, a plane-parallel plate filter such as a color filter or a powerless lens is not a rearmost lens. For instance, in the example 1 that will be described later, D2 is to be calculated by the following formula.

$$D2 = d14 + d15/n15 + d16/n16 + d17/n17$$

When falling below a lower limit value of conditional expression (5), a distance from the rearmost lens up to the image plane becomes excessively narrow. In this case, since a distance between the image pickup element and the oblique-viewing objective optical system becomes excessively narrow, adequate focus adjustment cannot be carried out at the time of assembling the oblique-viewing objective optical system. Consequently, the depth of the far-point side becomes shallower than the depth required originally.

When exceeding an upper limit value of conditional expression (5), since it is possible to secure adequately the distance from the rearmost lens up to the image plane, the focus adjustment at the time of assembling the oblique-viewing objective optical system is possible. However, since the distance from the rearmost lens up to the image plane becomes excessively long, a position of the image pickup element is separated away excessively from the oblique-viewing objective optical system. As a result, when the oblique-viewing objective optical system has been installed on the front-end portion of the endoscope, the oblique-viewing objective optical system and the image pickup element (hereinafter, referred to as the 'imaging system') are susceptible to interfere with other members. In order to avoid the interference, it is necessary to provide a clearance around the imaging system inside the endoscope. When the clearance is provided, the overall front-end portion of endoscope becomes large-sized.

It is preferable to satisfy the following conditional expression (4') instead of conditional expression (4).

$$2.4 < D1/f < 4.2 \quad (4')$$

It is preferable to satisfy the following conditional expression (5') instead of conditional expression (5).

$$1.1 < D2/f < 1.6 \quad (5')$$

Moreover, in the oblique-viewing objective optical system according to the present embodiment, it is preferable that the following conditional expression (6) is satisfied:

$$1.7 < D1/D2 < 3.1 \quad (6),$$

where,

D1 denotes the air-conversion length from the image-side surface of the negative lens in the front-side lens group up to the aperture stop, and D2 denotes the air-conversion length from an image-side surface of the rearmost lens in the rear-side lens group up to image plane.

Conditional expression (6) regulates a ratio of the of the air-conversion length from the image-side surface of the negative lens in the front-side lens group up to the aperture stop and the air-conversion length from the image-side surface of the rearmost lens in the rear-side lens group up to the image plane. By satisfying conditional expression (6), it is possible to optimize a balance of the two air-conversion lengths. As a result, it is possible to optimize a size of the imaging system in particular.

When falling below a lower limit value of conditional expression (6), the air-conversion length from the image-side surface of the negative lens in the front-side lens group up to the aperture stop becomes excessively short. In this case, since it becomes difficult to hold the frame member with jigs and tools for assembling, the assemblability is degraded.

When exceeding an upper limit value of conditional expression (6), the frame member becomes large-sized. Since it leads to large-sizing of the frame member holding the front-side lens group in particular, the outer diameter of the front-end portion of the endoscope becomes large.

Moreover, in the oblique-viewing objective optical system according to the present embodiment, it is preferable that the following conditional expression (7) is satisfied:

$$1.5 < f_3/f_2 < 3.1 \quad (7),$$

where, $f_2$ denotes a focal length of a positive lens in the rear-side lens group, and $f_3$ denotes a focal length of the cemented lens in the rear-side lens group.

Conditional expression (7) regulates the focal length of the positive lens in the rear-side lens group and the focal length of the cemented lens in the rear-side lens group. By satisfying conditional expression (7), it is possible to optimize a balance of the refractive power of the positive lens and the refractive power of the cemented lens.

When falling below a lower limit value of conditional expression (7), since the focal length of the cemented lens becomes short, the positive refractive power of the rear-side lens group becomes large. In this case, the image position comes excessively close to the rear-side lens group. Consequently, a distance necessary for focus adjustment is inadequate. As a result, the depth of the far-point side becomes shallower than the depth required originally. Moreover, since an amount of coma aberration that occurs at a peripheral portion of image becomes large, the optical performance is degraded.

Moreover, particularly, in the rear-side lens group, a balance of a refractive power of the overall positive lenses and a refractive power of the overall negative lenses is disrupted. As a result, a longitudinal chromatic aberration and chromatic aberration of magnification occur. Consequently, the optical performance is degraded.

When exceeding an upper limit value of conditional expression (7), since the focal length of the cemented lens becomes long, the positive refractive power in the rear-side lens group becomes small. In this case, the image position is separated apart excessively from the rear-side lens group. Consequently, the overall length of the optical system becomes long. Moreover, since the amount of coma that occurs in the peripheral portion of image becomes large, the optical performance is degraded.

Furthermore, particularly, in the rear-side lens group, the balance of the refractive power of the overall positive lenses and the refractive power of the overall negative lenses is disrupted. As a result, the longitudinal chromatic aberration and chromatic aberration of magnification occur. Consequently, the optical performance is degraded.

Moreover, in the oblique-viewing objective optical system according to the present embodiment, it is preferable that the following conditional expression (8) is satisfied:

$$1.1 < |R_c|/f < 2.1 \quad (8),$$

where, $R_c$ denotes a radius of curvature of a cemented surface of the cemented lens in the rear-side lens group, and f denotes the focal length of the overall oblique-viewing objective optical system.

When falling below a lower limit value of conditional expression (8), the radius of curvature of the cemented surface of the cemented lens becomes small. In this case, an edge thickness of the positive lens in the cemented lens becomes thin, and moreover, a sagittal plane becomes deep in the negative lens of the cemented lens. Consequently, workability of lenses is degraded.

When exceeding an upper limit value of conditional expression (8), the radius of curvature of the cemented surface of the cemented lens becomes large. In this case, since a refractive power of the cemented surface becomes small, correction of the chromatic aberration becomes difficult.

In conditional expression (8), although an absolute value of $R_c$ has been regulated, it is desirable that the value of $R_c$ is a negative value.

Moreover, in the oblique-viewing objective optical system according to the present embodiment, it is preferable that the following conditional expression (9) is satisfied:

$$-17° < TW < 0° \quad (9)$$

where,

TW denotes an angle of incidence of a light ray on the image plane when the image height is the maximum.

By satisfying conditional expression (9), it is possible to suppress the height of a light ray in the rear-side lens group to be low. Consequently, it is possible to make an outer diameter of lenses in the rear-side lens group small. Moreover, it is possible to make the rear-side lens group small-sized in a state of the frame member included therein.

Here, TW is an angle made by a principal light ray that reaches at the maximum image height with an axis parallel to an optical axis. The angle is let to be negative when the principal light ray that reaches the maximum image height is incident to be separating away gradually from the optical axis. Moreover, TW is an angle in air as a medium.

It is preferable that the following conditional expression (9') is satisfied instead of conditional expression (9).

$$-12° \leq TW \leq -5° \quad (9')$$

Moreover, in the oblique-viewing objective optical system according to the present embodiment, it is preferable that the optical path converting element is either a prism or a mirror.

Moreover, in the oblique-viewing objective optical system according to the present embodiment, it is possible to use a glass material having a high refractive index for the optical path converting element.

As described above, in the oblique-viewing objective optical system according to the present embodiment, the optical path converting element has been disposed on the object side of the aperture stop. According to such arrangement, it is possible to secure appropriately the length of the frame member holding the front-side lens group. However, in this arrangement, since the height of a light ray becomes high in the front-side negative lens in particular, the outer diameter of the front-side negative lens is susceptible to become large.

Therefore, it is preferable to use a glass material having a high refractive index for the optical path converting element. By doing so, since it is possible to make the air conversion length of the optical path converting element short, it is possible to suppress the height of a light ray at the front negative lens to be low.

Moreover, in the oblique-viewing objective optical system according to the present embodiment, it is possible to use a low-dispersion glass material for the positive lens in the cemented lens and a high-dispersion glass material for the negative lens in the cemented lens.

Generally, since Abbe number for a glass material having a high refractive index is not much large, dispersion becomes large in the glass material having a high refractive index. Therefore, even if it is possible to make short the air-conversion length of the optical path converting element by using a glass material having a high refractive index for the optical path converting element, an effect on the chromatic aberration remains.

For such reason, it is preferable to use a low-dispersion glass material for the positive lens in the cemented lens and a high-dispersion glass material for the negative lens in the cemented lens. Particularly for the negative lens in the cemented lens, it is preferable to use a glass material having an abnormal dispersibility. By doing so, it is possible to correct the chromatic aberration favorably. Furthermore, it is possible balance various aberrations in the oblique-viewing objective optical system.

Moreover, the angle of view of the oblique-viewing objective optical system is determined mainly by the refractive power of the front-side negative lens. Since an optical path converting element having a long path length in glass is to be disposed between the front-side negative lens and the aperture stop, the height of a light ray at the front-side negative lens becomes high. Consequently, the outer diameter of the negative lens becomes large, and the oblique-viewing objective optical system also becomes large-sized. However, on the other hand, since the radius of curvature of the front-side negative lens becomes large, the decentration aberration does not occur easily even when the front-side negative lens is decentered, and the optical performance is not degraded easily. For this reason, taking into consideration not only the outer diameter of lenses but also an effect on optical performance due to decentering of lens, it is necessary to have an optimum arrangement on the object side of the aperture stop.

Moreover, an endoscope for oblique viewing according to the present embodiment includes the abovementioned oblique-viewing objective optical system.

The oblique-viewing objective optical system according to the present embodiment has a small size and high performance. Therefore, by including such oblique-viewing objective optical system, it is possible to achieve a high-quality image and to realize the endoscope for oblique-viewing which has a front-end portion of which a diameter is thinned.

Moreover, the oblique-viewing objective optical system according to the present embodiment can be used in an endoscope apparatus. The endoscope apparatus includes at least the oblique-viewing objective optical system of the present embodiment and an image pickup element.

Prior to describing examples, a general idea of an oblique-viewing objective optical system of the present example will be described below. In diagrams showing cross-sectional arrangement of an oblique-viewing objective optical system of each example, the optical path converting element has been shown as a diagram in which a prism is unfolded. Therefore, the optical path converting element has been depicted as a plane-parallel plate.

Figure 6A:
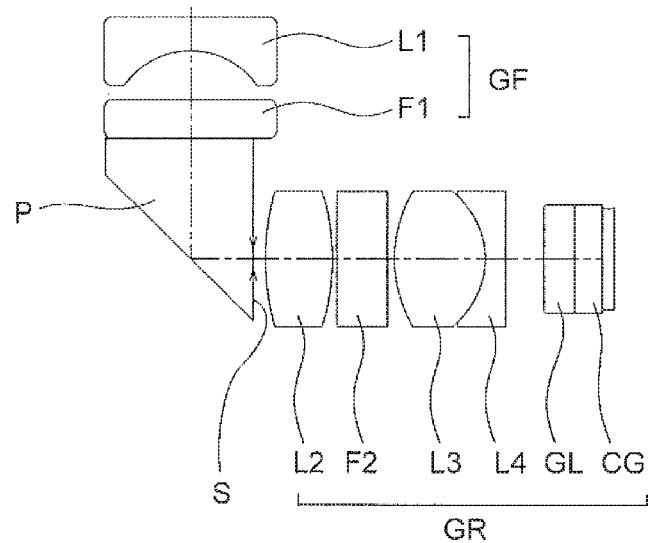
FIG. 6A is a diagram showing a cross-sectional arrangement of an oblique-viewing objective optical system according to the present example.

An example of a prism in a state of not being unfolded is shown in FIG. 6. FIG. 6A is a lens cross-sectional view when the prism is depicted in the state of not being unfolded. Here, an oblique-viewing objective optical system according to the example 1 has been exemplified as the oblique-viewing objective optical system of the present example. The oblique-viewing objective optical system of the present example includes a front-side lens group GF and a rear-side lens group GR disposed via a prism P, and an aperture stop S is disposed between the prism P and the rear-side lens group GR.

In other words, in the oblique-viewing objective optical system of the present example, the front-side lens group GF is disposed on an object side of the prism P, and the rear-side lens group GR is disposed on an image side of the prism. P. The front-side lens group GF has a negative refractive power and includes a lens L1 having a negative refractive power. The rear-side lens group GR has a positive refractive power, and includes a lens L2 having a positive refractive power and a cemented lens having a positive refractive power in which a lens L3 having a positive refractive power and a lens L4 having a negative refractive power have been cemented in this order.

When the prism P depicted as a plane-parallel plate is arranged as a one-time reflection prism, as shown in FIG. 6A, it is possible to arrange an objective optical system for side viewing that enables 90° lateral observation. Moreover, when a reflecting surface of the prism is set to an angle other than 45°, it is possible to form an objective optical system for front viewing or rear viewing for an angle other than 45°. Moreover, when the prism is arranged as a two-times reflection prism, it is also possible to form an objective optical system for front viewing of 45°.

Figure 6B:
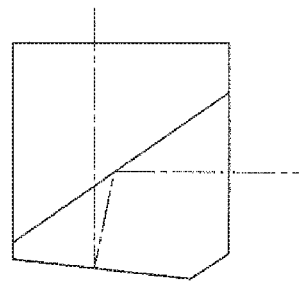
FIG. 6B and FIG. 6C are diagrams showing prisms.
Figure 6C:
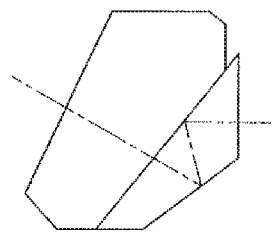

Furthermore, it is also possible to form the prism P by a plurality of prisms. In FIG. 6B, an arrangement that enables side-viewing with two prisms has been shown, and in FIG. 6C, an arrangement that enables front-viewing with two prisms has been shown.

Moreover, for a glass material of the prism P, it is preferable to use a glass material having a high refractive index of 1.8 and more. By doing so, it is possible to make the air-conversion length in the prism short.

A glass material of the negative lens L2 may be let to be sapphire. Sapphire being a material having an extremely high degree of hardness is strong against external shock. Therefore, a lens surface on the object side cannot have a scratch easily. By using sapphire, projection of a scratch on an image or flare due to scratch are hard to occur. A glass material for the negative lens is not restricted to sapphire. When a crystalline material having a high degree of hardness is used for the negative lens L1, a surface of the lens cannot have a scratch easily.

In the oblique-viewing objective optical system of the present example, two positive lenses are used. Both the positive lenses have a biconvex shape. Since the refractive index becomes low in a low-dispersion glass material, when a low-dispersion glass material is used for the positive lens, a radius of curvature of a lens surface becomes small. Consequently, problems such as an inability to secure adequately an edge thickness difference of a lens and an inability to secure a lens outer diameter having enough room for an effective aperture are susceptible to occur. Therefore, taking into consideration the workability of a lens, it is preferable to make an arrangement such that the radius of curvature of the positive lens does not become excessively small. For such reasons, it is preferable to use a glass material having a high refractive index of 1.7 and more for at least one of the positive lens L2 and the positive lens L3.

In a case of forming the positive lens L2 by a biconvex lens, it is preferable to let an object-side surface and an image-side surface to be surfaces having the same absolute value of a radius of curvature (hereinafter, referred to as the 'identical surfaces R'). By making such arrangement, since it is not necessary to distinguish a front and rear of a lens, assembling becomes easy.

When a biconvex lens is used for the positive lens L2, an absolute value of the radius of curvature of the object-side surface may be let to be larger than an absolute value of the radius of curvature of the image-side surface. By making such arrangement, aberration correction can be carried out easily.

Moreover, as a pixel pitch of the image pickup element becomes small, it is necessary to suppress the chromatic aberration to be small accordingly. In order to deal with this, it is preferable to use a high-dispersion glass material of refractive index 1.9 or more and Abbe number 25 or less for the negative lens L4 in the cemented lens. By doing so, it is possible to correct the chromatic aberration favorably.

Whereas, for the positive lens L3 in the cemented lens, it is preferable to use a low-dispersion glass material with Abbe number as large as possible. For example, it is preferable to use a glass material with Abbe number 50 or more for the positive lens L3.

Moreover, by disposing the cemented lens at a position near the image plane, the height of a light ray passing through the cemented lens becomes high. By disposing the cemented lens at a position where the height of a light ray is high, it is possible to correct the chromatic aberration of magnification favorably. Thus, disposing the cemented lens at a position near the image surface is effective in correction of particularly the chromatic aberration of magnification.

Moreover, examples of the plane-parallel plate other than prism provided in the oblique-viewing objective optical system of the present example are infra-red ray cut filters or color temperature conversion filters. These filters are to be used for correcting sensitivity of an image pickup element such as a CCD.

Moreover, a laser cut filter or a special function filter may be disposed in the oblique-viewing objective optical system. As a laser cut filter, filters for cutting laser light such as YAG laser and semiconductor laser are available. As a special function filter, a notch filter which cuts light rays of a specific wavelength region is available.

Moreover, for an optical filter, an absorbing filter, a reflecting filter, or a combination thereof may be used. Moreover, an antireflection film may be applied to a surface of an optical filter.

Moreover, a light transmitting surface of the prism may be provided with an interference film having an infrared light cut characteristic or a laser light cut characteristic.

Moreover, the plane-parallel plate filter disposed on the image-side surface of the oblique-viewing objective optical system of the present example is a cover glass and a glass lid used in an image pickup element. The image pickup element is to be fixed inside the frame member by holding a side surface and a front surface of the cover glass with the frame member.

Furthermore, by providing a filter F1 near the negative lens L1, it is possible to make small a volume of an air layer formed on the image-side surface of the negative lens L1. As a result, it is possible to reduce an effect of fogging due to dew formation on a lens surface.

Furthermore, the negative lens L1 and the filter F1 may be cemented. Moreover, the negative lens L1 and the filter F1 may be sealed by solder etc. to be air-tight. By doing so, it is possible to prevent occurrence of fogging more effectively.

Moreover, the number of lenses in the oblique-viewing objective optical system of the present invention is four which is small but the imaging performance is favorable. Thus, since it is possible to form the objective optical system by small number of lenses, it is possible to reduce cost.

Furthermore, in the oblique-viewing objective optical system of the present example, since an air space is narrow as compared to that in a conventional oblique-viewing objective optical system, the overall optical system is small-sized.

Examples of the present invention will be described below. In each aberration diagram, a horizontal axis indicates an amount of aberration. For spherical aberration, astigmatism, and chromatic aberration of magnification, the unit of amount of aberration is mm. Moreover, for distortion, the unit of amount of aberration is %. Moreover, IH denotes an image height and unit thereof is mm, and FNO denotes an F-number. Furthermore, the unit of a wavelength of aberration curve is nm.

Example 1

Figure 7A:
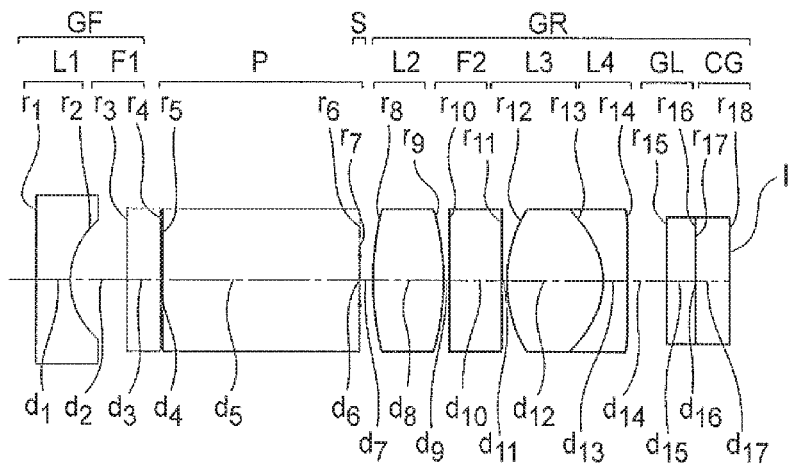
FIG. 7A is a diagram showing a cross-sectional arrangement of an oblique-viewing objective optical system according to an example 1.
Figures 7B, 7C, 7D, 7E:
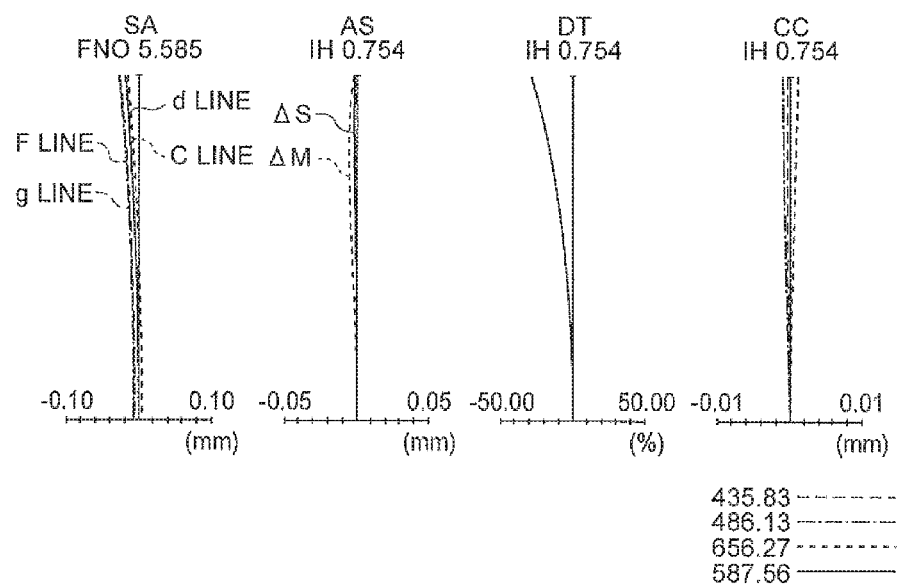
FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively of the example 1.

An oblique-viewing objective optical system according to the example 1 will be described below. FIG. 7A, FIG. 7B, FIG. 7C, FIG. 7D, and FIG. 7E are a diagram showing a cross-sectional arrangement and aberration diagrams of the oblique-viewing objective optical system according to the example 1, where, FIG. 7A shows a lens cross-section, FIG. 7B shows a spherical aberration (SA), FIG. 7C shows an astigmatism (AS), FIG. 7D shows a distortion (DT), and FIG. 7E shows a chromatic aberration of magnification (CC).

The oblique-viewing objective optical system according to the example 1, as shown in FIG. 7A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 2

Figure 8A:
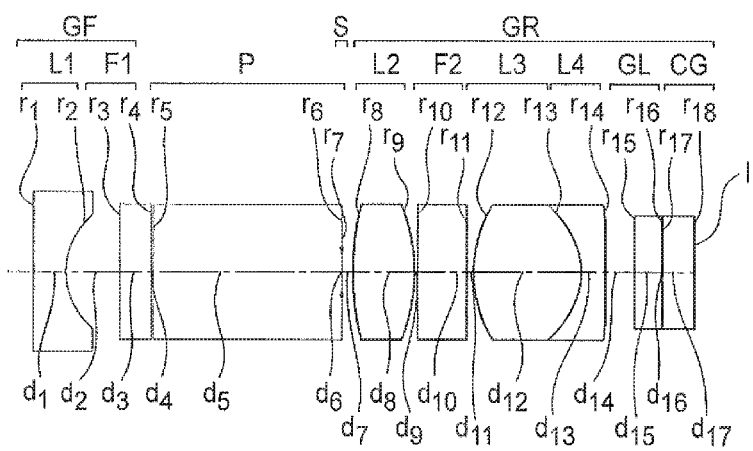
FIG. 8A is a diagram showing a cross-sectional arrangement of an oblique-viewing objective optical system according to an example 2.
Figures 8B, 8C, 8D, 8E:
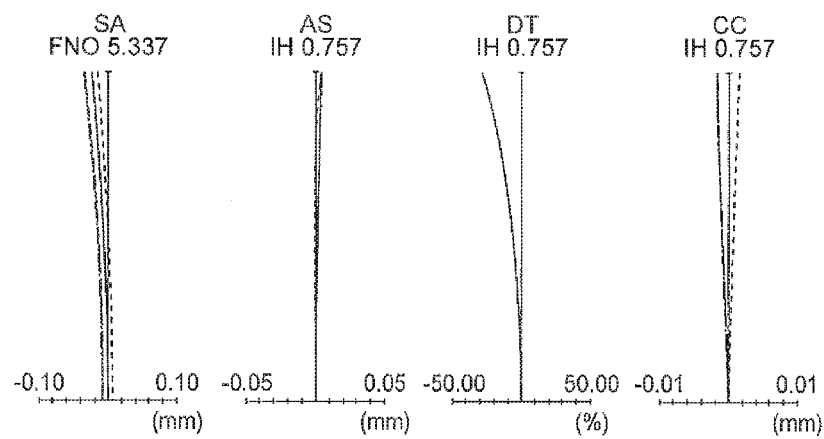
FIG. 8B, FIG. 8C, FIG. 8D, and FIG. 8E are aberration diagrams showing a spherical aberration (SA), an astigmatism (AS), a distortion (DT), and a chromatic aberration of magnification (CC) respectively of the example 2.

An oblique-viewing objective optical system according to an example 2 will be described below. FIG. 8A, FIG. 8B, FIG. 8C, FIG. 8D, and FIG. 8E are a diagram showing a cross-sectional arrangement and aberration diagrams of the oblique-viewing objective optical system according to the example 2, where, FIG. 8A shows a lens cross-section, FIG. 8B shows a spherical aberration (SA), FIG. 8C shows an astigmatism (AS), FIG. 8D shows a distortion (DT), and FIG. 8E shows a chromatic aberration of magnification (CC).

The oblique-viewing objective optical system according to the example 2, as shown in FIG. 8A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. An absolute value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

Example 3

Figure 9A:
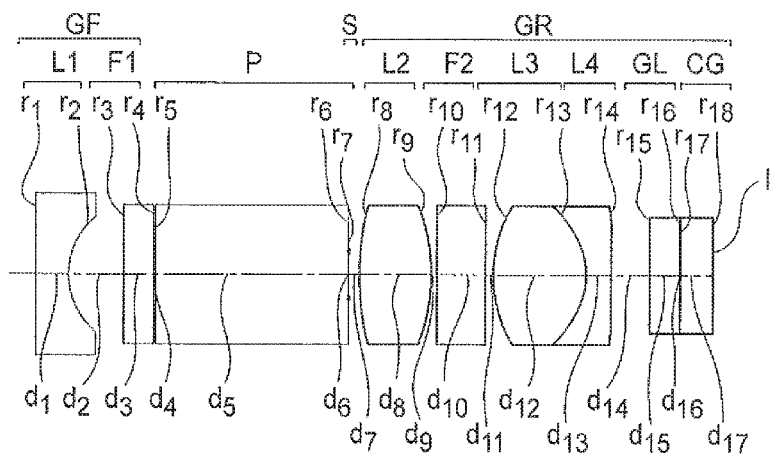
FIG. 9A is a diagram showing a cross-sectional arrangement of an oblique-viewing objective optical system according to an example 3.
Figures 9B, 9C, 9D, 9E:
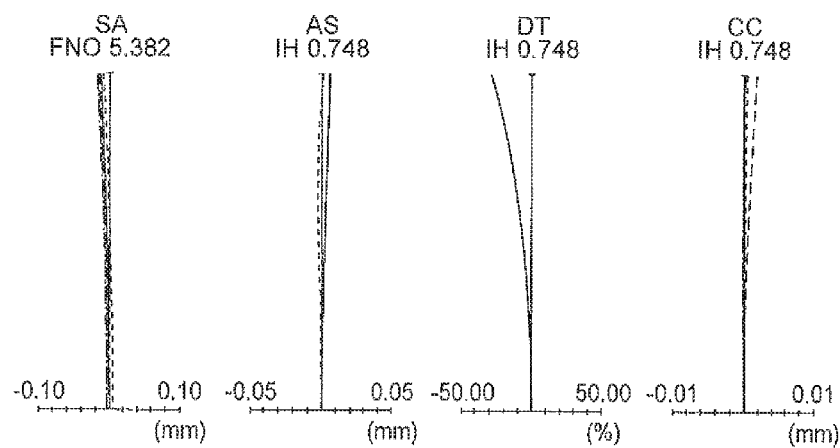
FIG. 9B, FIG. 9C, FIG. 9D, and FIG. 9E are aberration diagrams showing a spherical aberration (SA), an astigmatism (AS), a distortion (DT), and a chromatic aberration of magnification (CC) respectively of the example 3.

An oblique-viewing objective optical system according to an example 3 will be described below. FIG. 9A, FIG. 9B, FIG. 9C, FIG. 9D, and FIG. 9E are a diagram showing a cross-sectional arrangement and aberration diagrams of the oblique-viewing objective optical system according to the example 3, where, FIG. 9A shows a lens cross-section, FIG. 9B shows a spherical aberration (SA), FIG. 9C shows an astigmatism (AS), FIG. 9D shows a distortion (DT), and FIG. 9E shows a chromatic aberration of magnification (CC).

The oblique-viewing objective optical system according to the example 3, as shown in FIG. 9A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 4

Figure 10A:
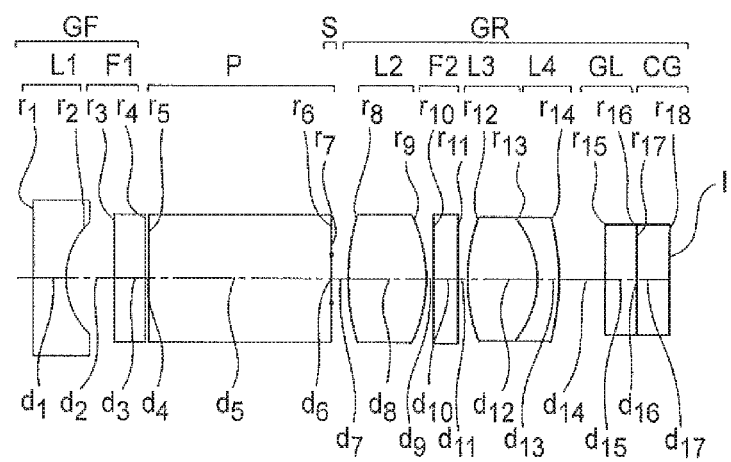
FIG. 10A is a diagram showing a cross-sectional arrangement of an oblique-viewing objective optical system according to an example 4.
Figures 10B, 10C, 10D, 10E:
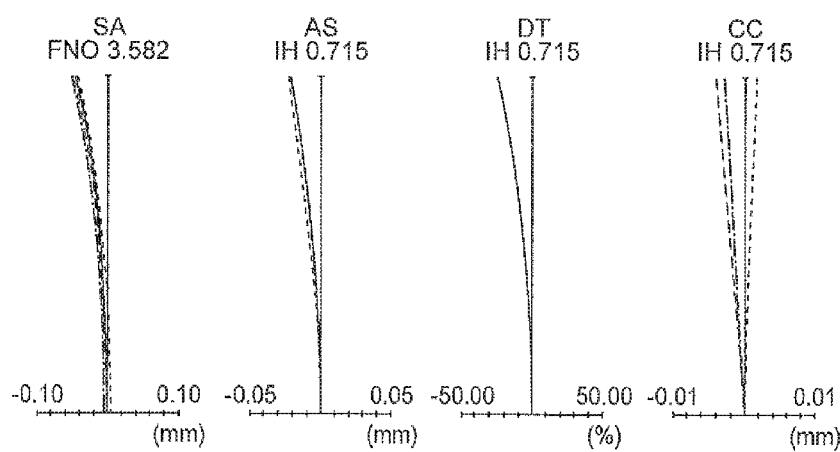
FIG. 10B, FIG. 10C, FIG. 10D, and FIG. 10E are aberration diagrams showing a spherical aberration (SA), an astigmatism (AS), a distortion (DT), and a chromatic aberration of magnification (CC) respectively of the example 4.

An oblique-viewing objective optical system according to an example 4 will be described below. FIG. 10A, FIG. 10B, FIG. 10C, FIG. 10D, and FIG. 10E are a diagram showing a cross-sectional arrangement and aberration diagrams of the oblique-viewing objective optical system according to the example 4, where, FIG. 10A shows a lens cross-section, FIG. 10B shows a spherical aberration (SA), FIG. 10C shows an astigmatism (AS), FIG. 10D shows a distortion (DT), and FIG. 10E shows a chromatic aberration of magnification (CC).

The oblique-viewing objective optical system according to the example 4, as shown in FIG. 10A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 5

Figure 11A:
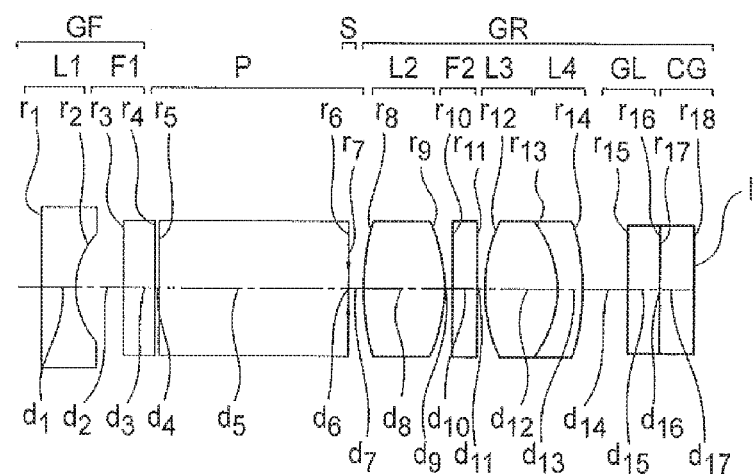
FIG. 11A is a diagram showing a cross-sectional arrangement of an oblique-viewing objective optical system according to an example 5.
Figures 11B, 11C, 11D, 11E:
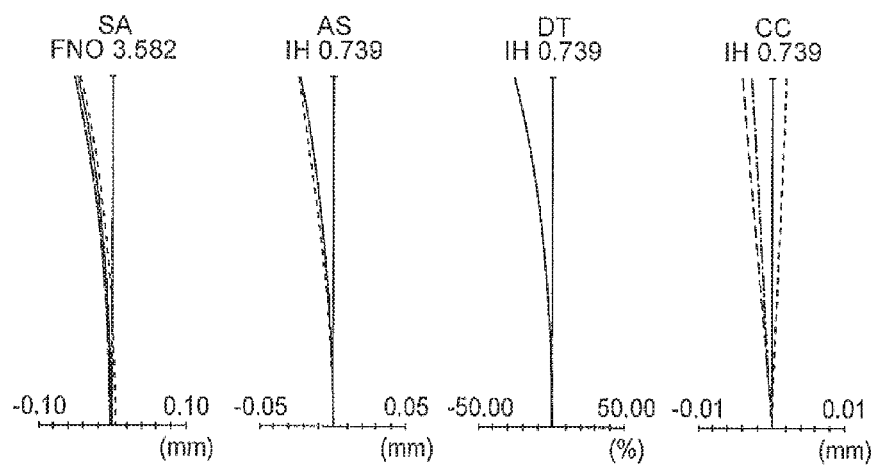
FIG. 11B, FIG. 11C, FIG. 11D, and FIG. 11E are aberration diagrams showing a spherical aberration (SA), an astigmatism (AS), a distortion (DT), and a chromatic aberration of magnification (CC) respectively of the example 5.

An oblique-viewing objective optical system according to an example 5 will be described below. FIG. 11A, FIG. 11B, FIG. 11C, FIG. 11D, and FIG. 11E are a diagram showing a cross-sectional arrangement and aberration diagrams of the oblique-viewing objective optical system according to the example 5, where, FIG. 11A shows a lens cross-section, FIG. 11B shows a spherical aberration (SA), FIG. 11C shows an astigmatism (AS), FIG. 11D shows a distortion (DT), and FIG. 11E shows a chromatic aberration of magnification (CC).

The oblique-viewing objective optical system according to the example 5, as shown in FIG. 11A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 6

Figure 12A:
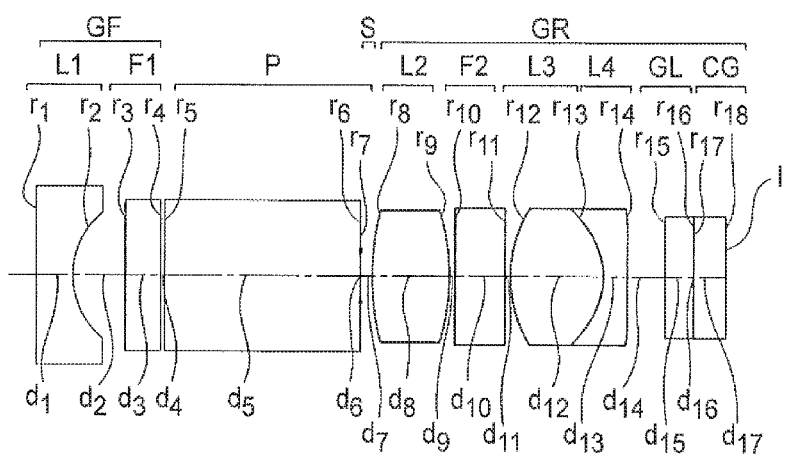
FIG. 12A is a diagram showing a cross-sectional arrangement of an oblique-viewing objective optical system according to an example 6.
Figures 12B, 12C, 12D, 12E:
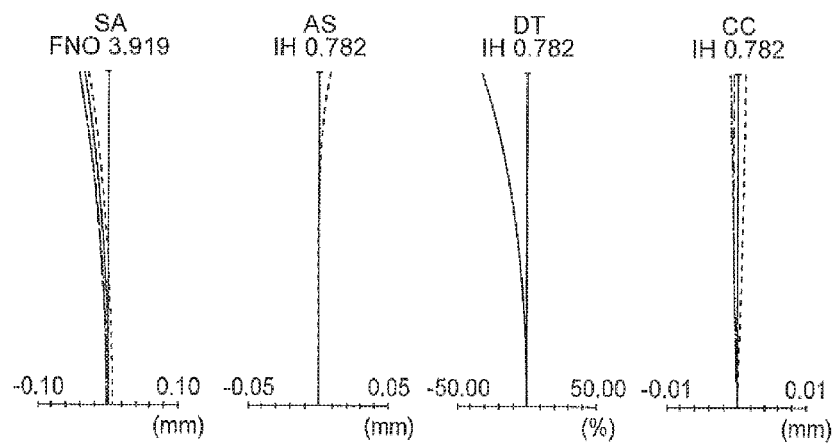
FIG. 12B, FIG. 12C, FIG. 12D, and FIG. 12E are aberration diagrams showing a spherical aberration (SA), an astigmatism (AS), a distortion (DT), and a chromatic aberration of magnification (CC) respectively of the example 6.

An oblique-viewing objective optical system according to an example 6 will be described below. FIG. 12A, FIG. 12B, FIG. 12C, FIG. 12D, and FIG. 12E are a diagram showing a cross-sectional arrangement and aberration diagrams of the oblique-viewing objective optical system according to the example 6, where, FIG. 12A shows a lens cross-section, FIG. 12B shows a spherical aberration (SA), FIG. 12C shows an astigmatism (AS), FIG. 12D shows a distortion (DT), and FIG. 12E shows a chromatic aberration of magnification (CC).

The oblique-viewing objective optical system according to the example 6, as shown in FIG. 12A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 7

Figure 13A:
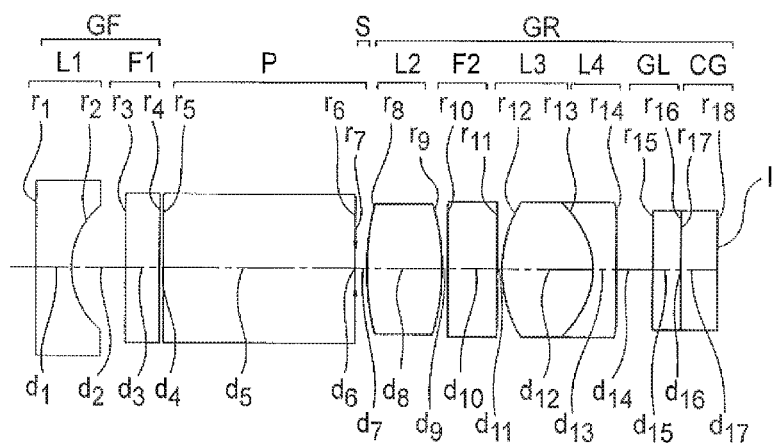
FIG. 13A is a diagram showing a cross-sectional arrangement of an oblique-viewing objective optical system according to an example 7.
Figures 13B, 13C, 13D, 13E:
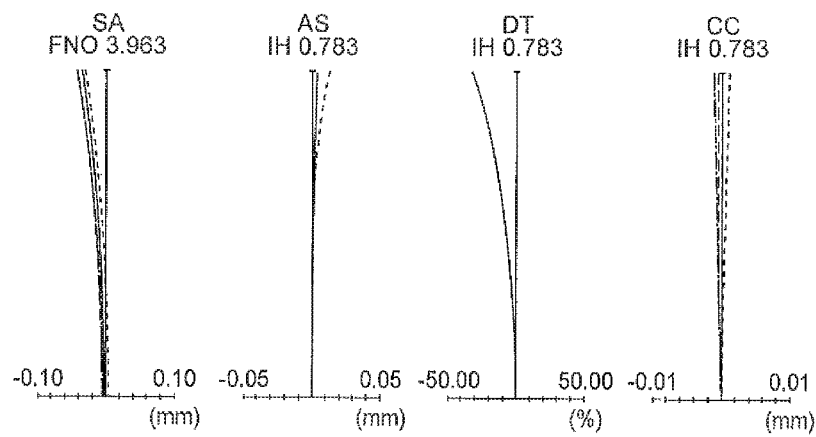
FIG. 13B, FIG. 13C, FIG. 13D, and FIG. 13E are aberration diagrams showing a spherical aberration (SA), an astigmatism (AS), a distortion (DT), and a chromatic aberration of magnification (CC) respectively of the example 7.

An oblique-viewing objective optical system according to an example 7 will be described below. FIG. 13A, FIG. 13B, FIG. 13C, FIG. 13D, and FIG. 13E are diagram showing a cross-sectional arrangement and aberration diagrams of the oblique-viewing objective optical system according to the example 7, where, FIG. 13A shows a lens cross-section, FIG. 13B shows a spherical aberration (SA), FIG. 13C shows an astigmatism (AS), FIG. 13D shows a distortion (DT), and FIG. 13E shows a chromatic aberration of magnification (CC).

The oblique-viewing objective optical system according to the example 7, as shown in FIG. 13A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 8

Figure 14A:
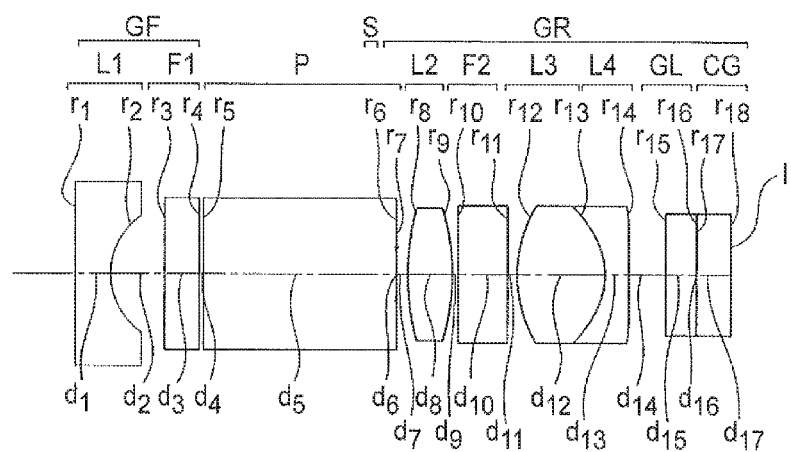
FIG. 14A is a diagram showing a cross-sectional arrangement of an oblique-viewing objective optical system according to an example 8.
Figures 14B, 14C, 14D, 14E:
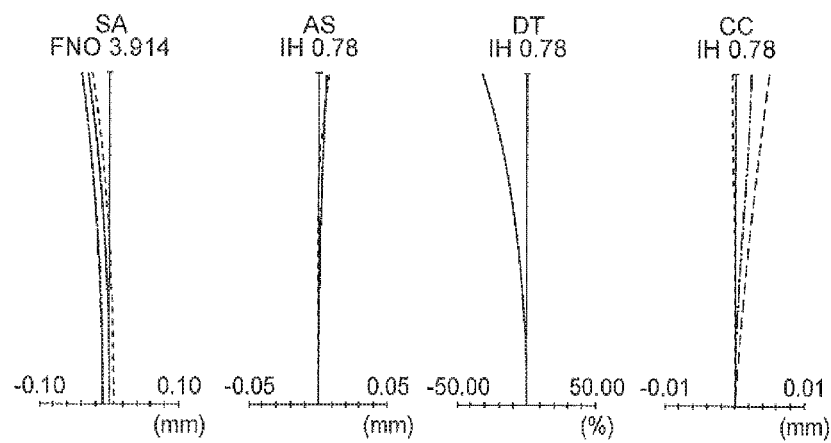
FIG. 14B, FIG. 14C, FIG. 14D, and FIG. 14E are aberration diagrams showing a spherical aberration (SA), an astigmatism (AS), a distortion (DT), and a chromatic aberration of magnification (CC) respectively of the example 8.

An oblique-viewing objective optical system according to an example 8 will be described below. FIG. 14A, FIG. 14B, FIG. 14C, FIG. 14D, and FIG. 14E are a diagram showing a cross-sectional arrangement and aberration diagrams of the oblique-viewing objective optical system according to the example 8, where, FIG. 14A shows a lens cross-section, FIG. 14B shows a spherical aberration (SA), FIG. 14C shows an astigmatism (AS), FIG. 14D shows a distortion (DT), and FIG. 14E shows a chromatic aberration of magnification (CC).

The oblique-viewing objective optical system according to the example 8, as shown in FIG. 14A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Sapphire is used for the planoconcave negative lens L1. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. An absolute value of a curvature of field of an object-side surface of the biconvex positive lens L2 is larger than an absolute value of a curvature of field of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

Example 9

Figure 15A:
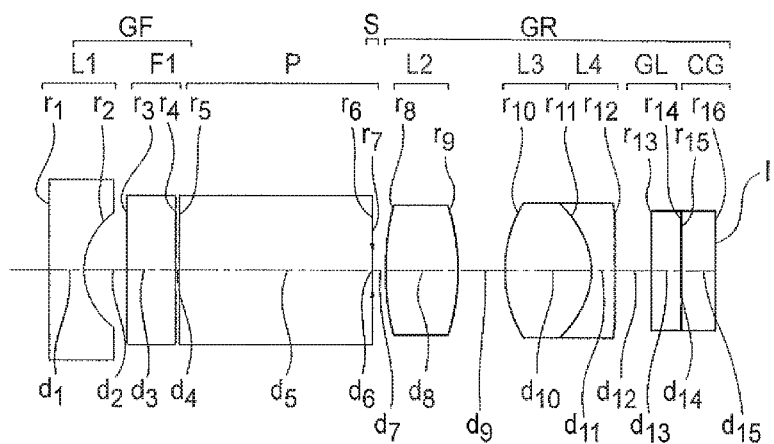
FIG. 15A is a diagram showing a cross-sectional arrangement of an oblique-viewing objective optical system according to an example 9.
Figures 15B, 15C, 15D, 15E:
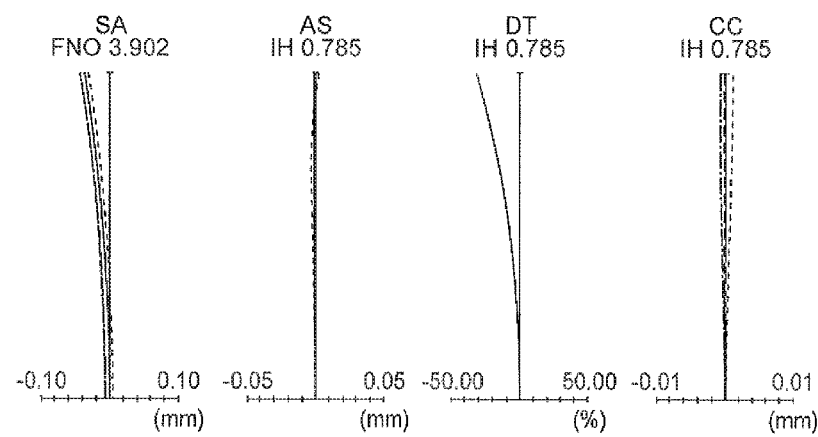
FIG. 15B, FIG. 15C, FIG. 15D, and FIG. 15E are aberration diagrams showing a spherical aberration (SA), an astigmatism (AS), a distortion (DT), and a chromatic aberration of magnification (CC) respectively of the example 9.

An oblique-viewing objective optical system according to an example 9 will be described below. FIG. 15A, FIG. 15B, FIG. 15C, FIG. 15D, and FIG. 15E are a diagram showing a cross-sectional arrangement and aberration diagrams of the oblique-viewing objective optical system according to the example 9, where, FIG. 15A shows a lens cross-section, FIG. 15B shows a spherical aberration (SA), FIG. 15C shows an astigmatism (AS), FIG. 15D shows a distortion (DT), and FIG. 15E shows a chromatic aberration of magnification (CC).

The oblique-viewing objective optical system according to the example 9, as shown in FIG. 15A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A glass lid GL and a cover glass CG are disposed in the rear-side lens group GR.

In the oblique-viewing objective optical system according to the present example, a function as an optical filter has been integrated in the filter F1. Therefore, there is only one optical filter disposed in the oblique-viewing objective optical system.

Example 10

Figure 16A:
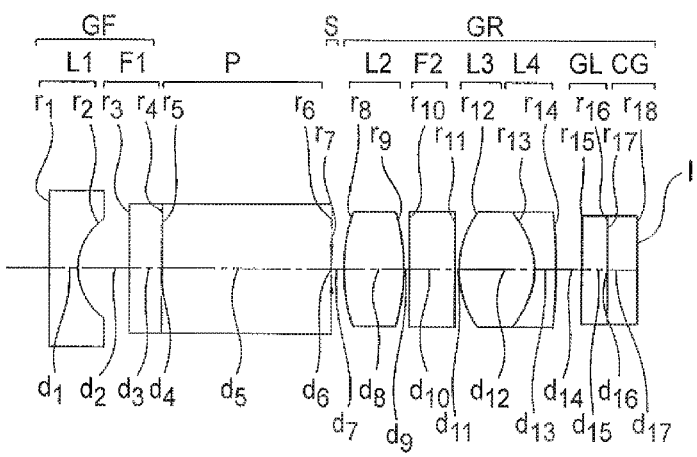
FIG. 16A is a diagram showing a cross-sectional arrangement of an oblique-viewing objective optical system according to an example 10.
Figures 16B, 16C, 16D, 16E:
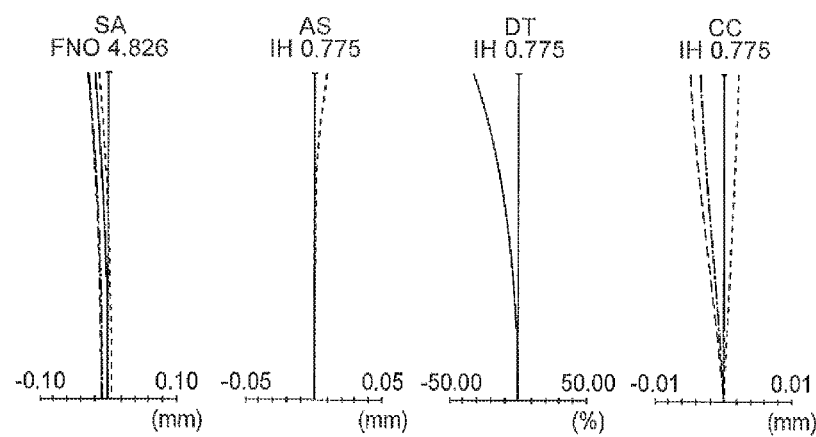
FIG. 16B, FIG. 16C, FIG. 16D, and FIG. 16E are aberration diagrams showing a spherical aberration (SA), an astigmatism (AS), a distortion (DT), and a chromatic aberration of magnification (CC) respectively of the example 10.

An oblique-viewing objective optical system according to an example 10 will be described below. FIG. 16A, FIG. 16B, FIG. 16C, FIG. 16D, and FIG. 16E are a diagram showing a cross-sectional arrangement and aberration diagrams of the oblique-viewing objective optical system according to the example 10, where, FIG. 16A shows a lens cross-section, FIG. 16B shows a spherical aberration (SA), FIG. 16C shows an astigmatism (AS), FIG. 16D shows a distortion (DT), and FIG. 16E shows a chromatic aberration of magnification (CC).

The oblique-viewing objective optical system according to the example 10, as shown in FIG. 16A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. Both surfaces of the biconvex positive lens L2 are the identical surfaces R. A filter F2, a glass lid GL, and a cover glass CG are disposed in the rear-side lens group GR. The filter F2 is disposed between the biconvex positive lens L2 and the cemented lens.

Example 11

Figure 17A:
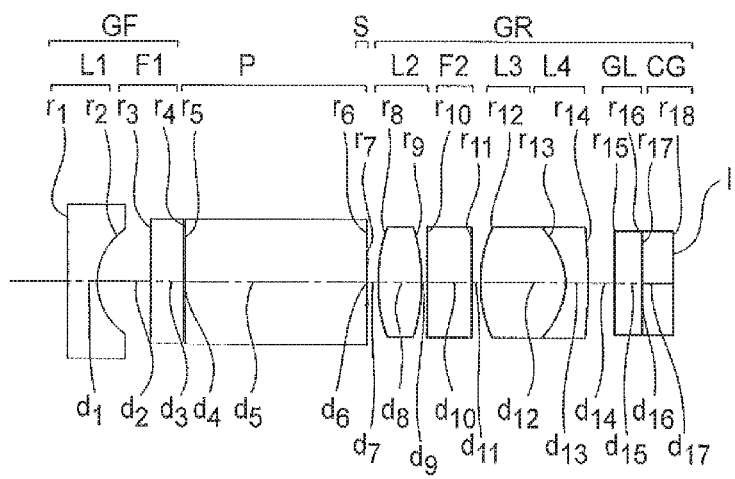
FIG. 17A is a diagram showing a cross-sectional arrangement of an oblique-viewing objective optical system according to an example 11.
Figures 17B, 17C, 17D, 17E:
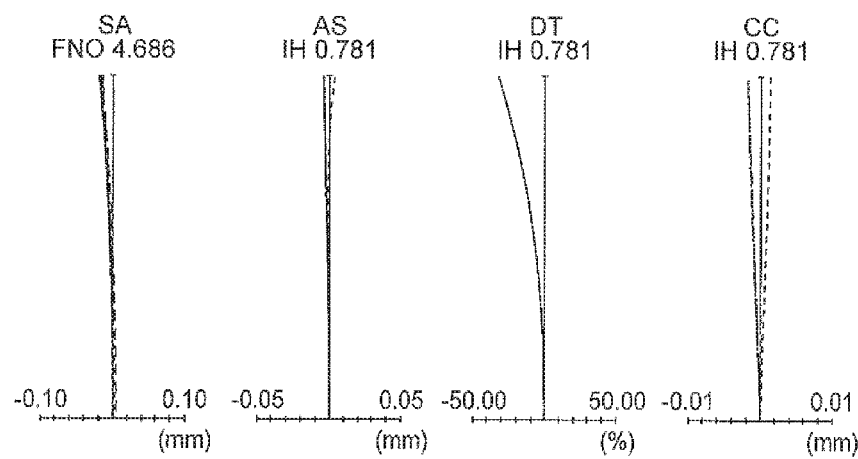
FIG. 17B, FIG. 17C, FIG. 17D, and FIG. 17E are aberration diagrams showing a spherical aberration (SA), an astigmatism (AS), a distortion (DT), and a chromatic aberration of magnification (CC) respectively of the example 11.

An oblique-viewing objective optical system according to an example 11 will be described below. FIG. 17A, FIG. 17B, FIG. 17C, FIG. 17D, and FIG. 17E are a diagram showing a cross-sectional arrangement and aberration diagrams of the oblique-viewing objective optical system according to the example 11, where, FIG. 17A shows a lens cross-section, FIG. 17B shows a spherical aberration (SA), FIG. 17C shows an astigmatism (AS), FIG. 17D shows a distortion (DT), and FIG. 17E shows a chromatic aberration of magnification (CC).

The oblique-viewing objective optical system according to the example 11, as shown in FIG. 17A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 forma cemented lens having a positive refractive power. An absoluter value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

Example 12

Figure 18A:
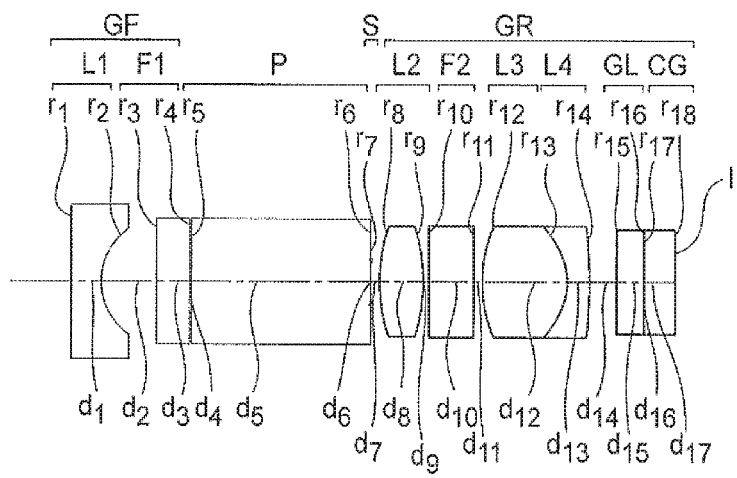
FIG. 18A is a diagram showing a cross-sectional arrangement of an oblique-viewing objective optical system according to an example 12.
Figures 18B, 18C, 18D, 18E:
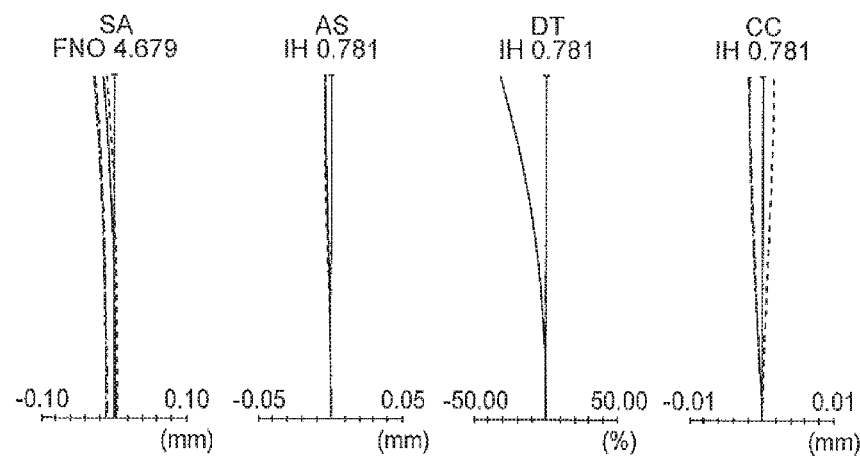
FIG. 18B, FIG. 18C, FIG. 18D, and FIG. 18E are aberration diagrams showing a spherical aberration (SA), an astigmatism (AS), a distortion (DT), and a chromatic aberration of magnification (CC) respectively of the example 12.

An oblique-viewing objective optical system according to an example 12 will be described below. FIG. 18A, FIG. 18B, FIG. 18C, FIG. 18D, and FIG. 18E are a diagram showing a cross-sectional arrangement and aberration diagrams of the oblique-viewing objective optical system according to the example 12, where, FIG. 18A shows a lens cross-section, FIG. 18B shows a spherical aberration (SA), FIG. 18C shows an astigmatism (AS), FIG. 18D shows a distortion (DT), and FIG. 18E shows a chromatic aberration of magnification (CC).

The oblique-viewing objective optical system according to the example 12, as shown in FIG. 18A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. An absolute value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

Example 13

Figure 19A:
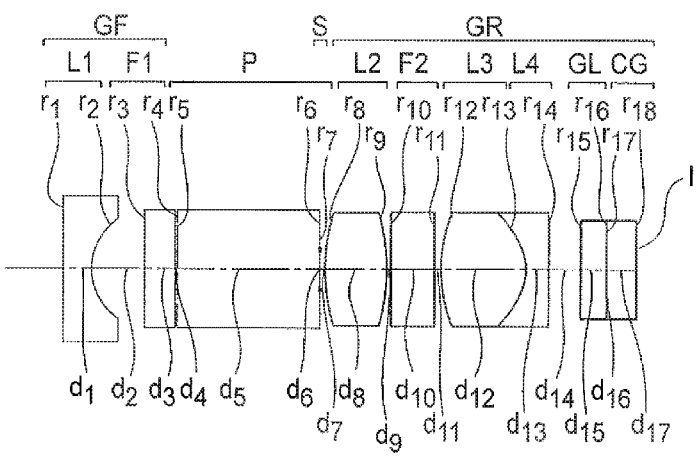
FIG. 19A is a diagram showing a cross-sectional arrangement of an oblique-viewing objective optical system according to an example 13.
Figures 19B, 19C, 19D, 19E:
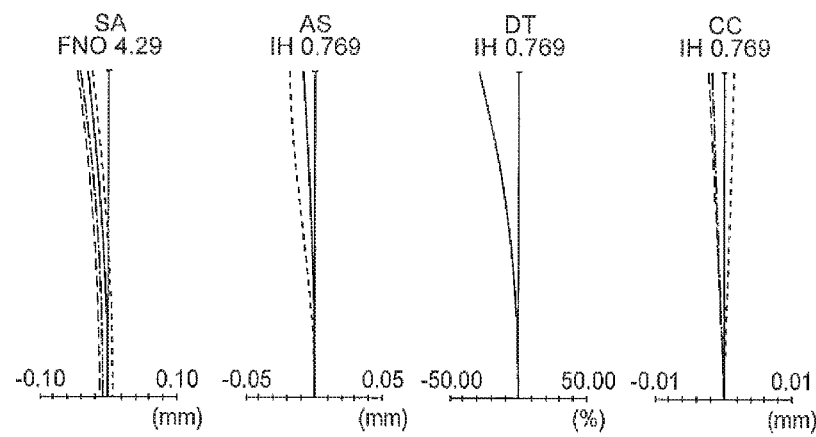
FIG. 19B, FIG. 19C, FIG. 19D, and FIG. 19E are aberration diagrams showing a spherical aberration (SA), an astigmatism (AS), a distortion (DT), and a chromatic aberration of magnification (CC) respectively of the example 13.

An oblique-viewing objective optical system according to an example 13 will be described below. FIG. 19A, FIG. 19B, FIG. 19C, FIG. 19D, and FIG. 19E are a diagram showing a cross-sectional arrangement and aberration diagrams of the oblique-viewing objective optical system according to the example 13, where, FIG. 19A shows a lens cross-section, FIG. 19B shows a spherical aberration (SA), FIG. 19C shows an astigmatism (AS), FIG. 19D shows a distortion (DT), and FIG. 19E shows a chromatic aberration of magnification (CC).

The oblique-viewing objective optical system according to the example 13, as shown in FIG. 19A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. An absolute value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

Example 14

Figure 20A:
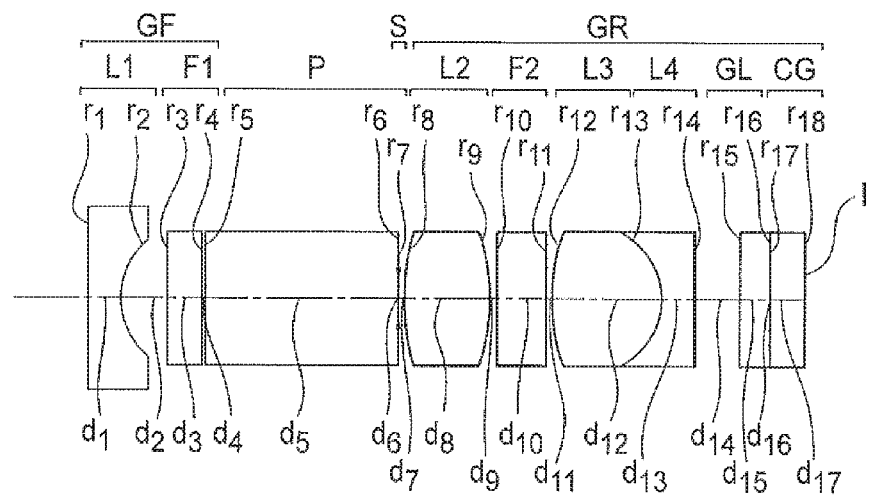
FIG. 20A is a diagram showing a cross-sectional arrangement of an oblique-viewing objective optical system according to an example 14.
Figures 20B, 20C, 20D, 20E:
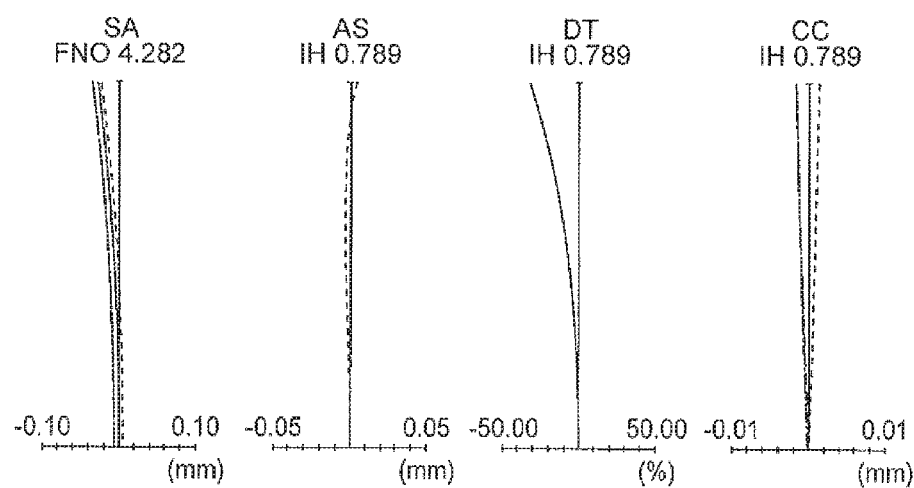
FIG. 20B, FIG. 20C, FIG. 20D, and FIG. 20E are aberration diagrams showing a spherical aberration (SA), an astigmatism (AS), a distortion (DT), and a chromatic aberration of magnification (CC) respectively of the example 14.

An oblique-viewing objective optical system according to an example 14 will be described below. FIG. 20A, FIG. 20B, FIG. 20C, FIG. 20D, and FIG. 20E are a diagram showing a cross-sectional arrangement and aberration diagrams of the oblique-viewing objective optical system according to the example 14, where, FIG. 20A shows a lens cross-section, FIG. 20B shows a spherical aberration (SA), FIG. 20C shows an astigmatism (AS), FIG. 20D shows a distortion (DT), and FIG. 20E shows a chromatic aberration of magnification (CC).

The oblique-viewing objective optical system according to the example 14, as shown in FIG. 20A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed between the planoconcave negative lens L1 and the optical path converting element P, in the front-side lens group GF.

The optical path converting element P is disposed between the front-side lens group GF and the rear-side lens group GR. The optical path converting element P is a prism. A glass material having a low refractive index of about 1.5 is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a planoconcave negative lens L4. Here, the biconvex positive lens L3 and the planoconcave negative lens L4 form a cemented lens having a positive refractive power. An absolute value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

In the oblique-viewing objective optical system according to the present example, a glass material having a low refractive index is used for the prism. Consequently, it is necessary to widen a distance (air conversion length) between the front-side lens group GF and the rear-side lens group GR to be able to dispose the prism. However, a glass material having a low refractive index has dispersion lower than that of a glass material having a high refractive index. Therefore, even without using a glass material with Abbe number less than 20 having a high refractive index and abnormal dispersion, correction of the chromatic aberration is possible. In the present example, a glass material having a refractive index of about 1.8 and Abbe number of about 22 has been used.

Moreover, when a glass material having a low refractive index is used for the optical path converting element (prism), since the distance between the front-side lens group and the rear-side lens group becomes long as compared to a case of a glass material having a high refractive index, an outer diameter of the negative lens becomes large. However, since the optical path converting element is made short in the oblique-viewing objective optical system according to the present example, a diameter of lenses in the front-side lens group is about same as in other examples.

Moreover, a difference in a refractive index of the biconvex positive lens L3 and a refractive index of the planoconcave negative lens L4 in the cemented lens is approximately 0.07 which is small. Furthermore, an image-side surface of the planoconcave negative lens L4 is a flat surface. Therefore, workability of the lens is favorable, and it is easy to distinguish a front and rear of the lens while assembling.

Example 15

Figure 21A:
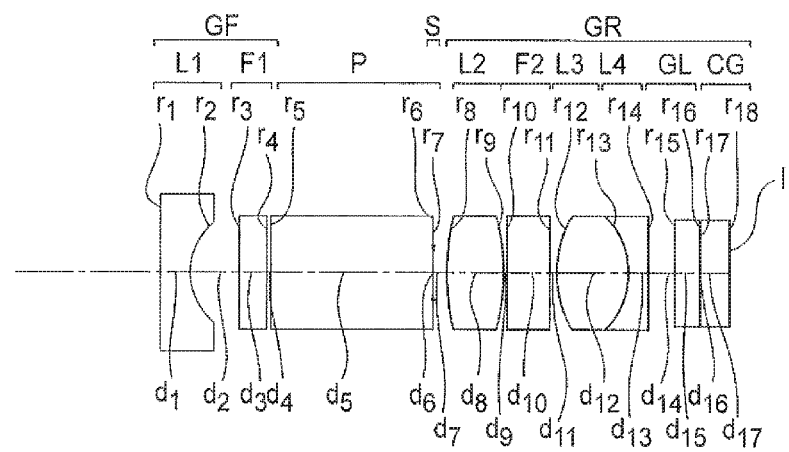
FIG. 21A is a diagram showing a cross-sectional arrangement of an oblique-viewing objective optical system according to an example 15.
Figures 21B, 21C, 21D, 21E:
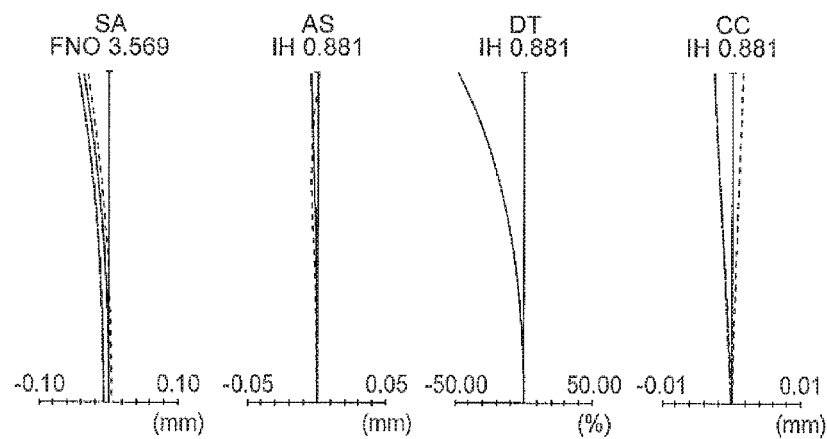
FIG. 21B, FIG. 21C, FIG. 21D, and FIG. 21E are aberration diagrams showing a spherical aberration (SA), an astigmatism (AS), a distortion (DT), and a chromatic aberration of magnification (CC) respectively of the example 15.

An oblique-viewing objective optical system according to an example 15 will be described below. FIG. 21A, FIG. 21B, FIG. 21C, FIG. 21D, and FIG. 21E are a diagram showing a cross-sectional arrangement and aberration diagrams of the oblique-viewing optical system according to the example 15, where, FIG. 21A shows a lens cross-section, FIG. 21B shows a spherical aberration (SA), FIG. 21C shows an astigmatism (AS), FIG. 21D shows a distortion (DT), and FIG. 21E shows a chromatic aberration of magnification (CC).

The oblique-viewing objective optical system according to the example 15, as shown in FIG. 21A, includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a flat surface. Moreover, a filter F1 is disposed in the front-side lens group GF. The filter F1 is disposed between the planoconcave negative lens L1 and the optical path converting element P.

The optical path converting element P is disposed between the front-side lens group GF and the rear-side lens group GR. The optical path converting element P is a prism. A glass material having a high refractive index of 1.8 or more is used for the prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L2, a biconvex positive lens L3, and a negative meniscus lens L4 having a convex surface directed toward an image side. Here, the biconvex positive lens L3 and the negative meniscus lens L4 form a cemented lens having a positive refractive power. An absolute value of a radius of curvature of an object-side surface of the biconvex positive lens L2 is larger than an absolute value of a radius of curvature of an image-side surface of the biconvex positive lens L2. A filter F2, a glass lid GL, and a cover glass CG are disposed in the rear-side lens group GR. The filter F2 is disposed between the biconvex positive lens L2 and the cemented lens.

In the oblique-viewing objective optical system according to the present example, although an angle of view is widened to 120°, by using a glass material having a high refractive index of 1.8 or more for the prism, (an absolute value of) a radius of curvature of an image-side surface of the planoconcave negative lens L1 is not let to be small. Moreover, with the F-number of about 3.6, it is a fast and high performance oblique-viewing objective optical system.

As described heretofore, the oblique-viewing objective optical system of each example includes the front-side lens group disposed on the object side of the prism and the rear-side lens group disposed on the image side of the prism. The front-side lens group has a negative refractive power and includes the lens having a negative refractive power, and the rear-side lens group has a positive refractive power and includes the lens having a positive refractive power and a cemented lens having a positive refractive power. The cemented lens includes the lens having a positive refractive power and a lens having a negative refractive power cemented in this order, and the aperture stop is provided between the prism and the rear-side lens group.

The oblique-viewing objective optical system according to each example has the optimum lens arrangement with the optical performance improved in responding small-sizing and increasing number of pixels of the image pickup element, and such arrangement also contributes to thinning of diameter of the front-end portion of endoscope. Furthermore, since the oblique-viewing objective optical system of each example satisfies each conditional expression, various aberrations are corrected favorably.

Numerical data of each example described above is shown below. In symbols, r denotes radius of curvature of each surface, d denotes a thickness of each optical member or air distance, nd denotes a refractive index of each optical member for d-line, vd denotes an Abbe number for each optical member, f denotes a focal length of the overall oblique-viewing objective optical system, IH denotes an image height, ω denotes a half angle of view, $f_F$ denotes a focal length of the front-side lens group, $f_R$ denotes a focal length of the rear-side lens group, D1 denotes an air-conversion length from an image-side surface of the negative lens in the front-side lens group up to the aperture stop, D2 denotes an air-conversion length from an image-side surface of the rearmost lens in the rear-side lens group up to the image plane, $f_2$ denotes a focal length of a positive lens in the rear-side lens group, $f_3$ denotes a focal length of the cemented lens in the rear-side lens group, and TW denotes an angle of incidence of a light ray on the image plane when the image height is the maximum. Moreover, unit of r, d, IH, air-conversion length, and each focal length is mm.

Example 1

Unit mm

Surface data

| Surface no. | r | d | nd | vd |
| --- | --- | --- | --- | --- |
| 1 | ∞ | 0.5824 | 1.88300 | 40.76 |
| 2 | 1.3715 | 0.9318 | | |
| 3 | ∞ | 0.5824 | 1.51633 | 64.14 |
| 4 | ∞ | 0.0582 | | |
| 5 | ∞ | 3.3735 | 1.88300 | 40.76 |
| 6 | ∞ | 0 | | |
| 7(Stop) | ∞ | 0.1893 | | |
| 8 | 3.9034 | 1.2667 | 1.75500 | 52.32 |
| 9 | −3.9034 | 0.0874 | | |
| 10 | ∞ | 0.8736 | 1.52100 | 65.13 |
| 11 | ∞ | 0.1165 | | |
| 12 | 2.4271 | 1.6452 | 1.58913 | 61.14 |
| 13 | −1.5608 | 0.4368 | 1.92286 | 18.90 |
| 14 | −18.2083 | 0.6471 | | |
| 15 | ∞ | 0.4805 | 1.88300 | 40.76 |
| 16 | ∞ | 0.0146 | 1.51300 | 64.00 |
| 17 | ∞ | 0.5824 | 1.61062 | 50.49 |
| 18 (Image plane) | ∞ | 0 | | |

Various data

| IH | 0.754 |
| --- | --- |
| ω | 46.963 |
| Fno | 5.585 |

Example 2

Unit mm

Surface data

| Surface no. | r | d | nd | vd |
| --- | --- | --- | --- | --- |
| 1 | ∞ | 0.5849 | 1.88300 | 40.76 |
| 2 | 1.3488 | 0.9358 | | |
| 3 | ∞ | 0.5849 | 1.51633 | 64.14 |
| 4 | ∞ | 0.0585 | | |
| 5 | ∞ | 3.3878 | 1.88300 | 40.76 |
| 6 | ∞ | 0 | | |
| 7(Stop) | ∞ | 0.1901 | | |
| 8 | 4.7265 | 1.1067 | 1.72916 | 54.68 |
| 9 | −3.3389 | 0.0731 | | |
| 10 | ∞ | 0.8773 | 1.52100 | 65.13 |
| 11 | ∞ | 0.1024 | | |
| 12 | 2.5638 | 1.9281 | 1.58913 | 61.14 |
| 13 | −1.6295 | 0.4533 | 1.92286 | 18.90 |
| 14 | −17.7766 | 0.5258 | | |
| 15 | ∞ | 0.4825 | 1.51633 | 64.14 |
| 16 | ∞ | 0.0146 | 1.51300 | 64.00 |

Example 3

| Unit mm | | | | |
|---|---|---|---|---|
| Surface data | | | | |
| Surface no. | r | d | nd | vd |
| 1 | ∞ | 0.5774 | 1.88300 | 40.76 |
| 2 | 1.2959 | 0.9238 | | |
| 3 | ∞ | 0.5774 | 1.51633 | 64.14 |
| 4 | ∞ | 0.0577 | | |
| 5 | ∞ | 3.3446 | 1.88300 | 40.76 |
| 6 | ∞ | 0 | | |
| 7(Stop) | ∞ | 0.1877 | | |
| 8 | 4.2060 | 1.2820 | 1.77250 | 49.60 |
| 9 | −4.2060 | 0.0866 | | |
| 10 | ∞ | 0.8661 | 1.52100 | 65.13 |
| 11 | ∞ | 0.1155 | | |
| 12 | 2.2312 | 1.6570 | 1.58913 | 61.14 |
| 13 | −1.4930 | 0.4330 | 1.92286 | 18.90 |
| 14 | −25.0484 | 0.6461 | | |
| 15 | ∞ | 0.5774 | 1.51633 | 64.14 |
| 16 | ∞ | 0.0144 | 1.51300 | 64.00 |
| 17 | ∞ | 0.5774 | 1.61062 | 50.49 |
| 18 (Image plane) | ∞ | 0 | | |

| Various data | |
|---|---|
| IH | 0.748 |
| ω | 46.852 |
| Fno | 5.382 |

Example 4

| Unit mm | | | | |
|---|---|---|---|---|
| Surface data | | | | |
| Surface no. | r | d | nd | vd |
| 1 | ∞ | 0.5574 | 1.88300 | 40.76 |
| 2 | 1.4786 | 0.8083 | | |
| 3 | ∞ | 0.5574 | 1.51633 | 64.14 |
| 4 | ∞ | 0.0557 | | |
| 5 | ∞ | 3.2290 | 1.88300 | 40.76 |
| 6 | ∞ | 0 | | |
| 7(Stop) | ∞ | 0.2508 | | |
| 8 | 3.4826 | 1.3936 | 1.72916 | 54.68 |
| 9 | −3.4826 | 0.1394 | | |
| 10 | ∞ | 0.4320 | 1.51401 | 75.26 |
| 11 | ∞ | 0.1394 | | |
| 12 | 2.6785 | 1.2542 | 1.51633 | 64.15 |
| 13 | −1.6389 | 0.3763 | 1.92286 | 18.90 |
| 14 | −4.6881 | 0.7878 | | |
| 15 | ∞ | 0.5574 | 1.51633 | 64.14 |
| 16 | ∞ | 0.0139 | 1.51300 | 53.00 |
| 17 | ∞ | 0.5574 | 1.50510 | 63.26 |
| 18 (Image plane) | ∞ | 0 | | |

| Various data | |
|---|---|
| IH | 0.715 |
| ω | 44.041 |
| Fno | 3.582 |

Example 5

| Unit mm | | | | |
|---|---|---|---|---|
| Surface data | | | | |
| Surface no. | r | d | nd | vd |
| 1 | ∞ | 0.5574 | 1.88300 | 40.76 |
| 2 | 1.4786 | 0.8083 | | |
| 3 | ∞ | 0.5574 | 1.51633 | 64.14 |
| 4 | ∞ | 0.0557 | | |
| 5 | ∞ | 3.2290 | 1.88300 | 40.76 |
| 6 | ∞ | 0 | | |
| 7(Stop) | ∞ | 0.2508 | | |
| 8 | 3.4826 | 1.3936 | 1.72916 | 54.68 |
| 9 | −3.4826 | 0.1394 | | |
| 10 | ∞ | 0.4320 | 1.51401 | 75.26 |
| 11 | ∞ | 0.1394 | | |
| 12 | 2.6785 | 1.2542 | 1.51633 | 64.15 |
| 13 | −1.6389 | 0.3763 | 1.92286 | 18.90 |
| 14 | −4.6881 | 0.7921 | | |
| 15 | ∞ | 0.5574 | 1.51633 | 64.14 |
| 16 | ∞ | 0.0139 | 1.50808 | 63.26 |
| 17 | ∞ | 0.5574 | 1.52275 | 55.29 |
| 18 (Image plane) | ∞ | 0 | | |

| Various data | |
|---|---|
| IH | 0.739 |
| ω | 45.823 |
| Fno | 3.582 |

Example 6

| Unit mm | | | | |
|---|---|---|---|---|
| Surface data | | | | |
| Surface no. | r | d | nd | vd |
| 1 | ∞ | 0.6039 | 1.88300 | 40.76 |
| 2 | 1.3977 | 0.9902 | | |
| 3 | ∞ | 0.6039 | 1.51633 | 64.14 |
| 4 | ∞ | 0.0604 | | |
| 5 | ∞ | 3.4984 | 1.88300 | 40.76 |
| 6 | ∞ | 0 | | |
| 7(Stop) | ∞ | 0.2202 | | |
| 8 | 4.1101 | 1.3586 | 1.75500 | 52.32 |
| 9 | −4.1101 | 0.0906 | | |
| 10 | ∞ | 0.9059 | 1.52100 | 65.13 |
| 11 | ∞ | 0.1208 | | |
| 12 | 2.4546 | 1.6388 | 1.58913 | 61.14 |
| 13 | −1.6488 | 0.4530 | 1.92286 | 18.90 |
| 14 | −15.7302 | 0.6285 | | |
| 15 | ∞ | 0.5285 | 1.51633 | 64.14 |
| 16 | ∞ | 0.0151 | 1.51300 | 64.00 |

-continued

| Unit mm | | | | |
|---|---|---|---|---|
| 17 | ∞ | 0.6039 | 1.61062 | 50.49 |
| 18 (Image plane) | ∞ | 0 | | |

| Various data | |
|---|---|
| IH | 0.782 |
| ω | 49.682 |
| Fno | 3.919 |

Example 7

| Unit mm | | | | |
|---|---|---|---|---|
| Surface data | | | | |
| Surface no. | r | d | nd | νd |
| 1 | ∞ | 0.6047 | 1.88300 | 40.76 |
| 2 | 1.4045 | 0.9860 | | |
| 3 | ∞ | 0.6047 | 1.51633 | 64.14 |
| 4 | ∞ | 0.0605 | | |
| 5 | ∞ | 3.5027 | 1.80610 | 40.92 |
| 6 | ∞ | 0 | | |
| 7(Stop) | ∞ | 0.2150 | | |
| 8 | 4.1478 | 1.3511 | 1.75500 | 52.32 |
| 9 | −4.1478 | 0.0907 | | |
| 10 | ∞ | 0.9070 | 1.52100 | 65.13 |
| 11 | ∞ | 0.1209 | | |
| 12 | 2.4738 | 1.6527 | 1.58913 | 61.14 |
| 13 | −1.6436 | 0.4535 | 1.92286 | 18.90 |
| 14 | −16.3751 | 0.6376 | | |
| 15 | ∞ | 0.5291 | 1.51633 | 64.14 |
| 16 | ∞ | 0.0151 | 1.51300 | 64.00 |
| 17 | ∞ | 0.6047 | 1.61062 | 50.49 |
| 18 (Image plane) | ∞ | 0 | | |

| Various data | |
|---|---|
| IH | 0.783 |
| ω | 49.783 |
| Fno | 3.963 |

Example 8

| Unit mm | | | | |
|---|---|---|---|---|
| Surface data | | | | |
| Surface no. | r | d | nd | νd |
| 1 | ∞ | 0.6025 | 1.76820 | 71.79 |
| 2 | 1.2469 | 0.9706 | | |
| 3 | ∞ | 0.6025 | 1.51633 | 64.14 |
| 4 | ∞ | 0.0603 | | |
| 5 | ∞ | 3.4902 | 1.80610 | 40.92 |
| 6 | ∞ | 0 | | |
| 7(Stop) | ∞ | 0.2007 | | |
| 8 | 4.3747 | 0.8191 | 1.75500 | 52.32 |
| 9 | −3.9694 | 0.0904 | | |
| 10 | ∞ | 0.9038 | 1.52100 | 65.13 |
| 11 | ∞ | 0.1205 | | |
| 12 | 2.3851 | 1.6115 | 1.58913 | 61.14 |
| 13 | −1.6658 | 0.4519 | 1.92286 | 18.90 |
| 14 | −17.1437 | 0.6244 | | |
| 15 | ∞ | 0.5272 | 1.51633 | 64.14 |
| 16 | ∞ | 0.0151 | 1.51300 | 64.00 |

-continued

| Unit mm | | | | |
|---|---|---|---|---|
| 17 | ∞ | 0.6025 | 1.61062 | 50.49 |
| 18 (Image plane) | ∞ | 0 | | |

| Various data | |
|---|---|
| IH | 0.78 |
| ω | 49.868 |
| Fno | 3.914 |

Example 9

| Unit mm | | | | |
|---|---|---|---|---|
| Surface data | | | | |
| Surface no. | r | d | nd | νd |
| 1 | ∞ | 0.6063 | 1.88300 | 40.76 |
| 2 | 1.4043 | 0.7963 | | |
| 3 | ∞ | 0.9094 | 1.52100 | 65.13 |
| 4 | ∞ | 0.0606 | | |
| 5 | ∞ | 3.5118 | 1.88300 | 40.76 |
| 6 | ∞ | 0 | | |
| 7(Stop) | ∞ | 0.2215 | | |
| 8 | 4.1211 | 1.3238 | 1.75500 | 52.32 |
| 9 | −4.1211 | 0.8039 | | |
| 10 | 2.4518 | 1.6393 | 1.58913 | 61.14 |
| 11 | −1.6490 | 0.4547 | 1.92286 | 18.90 |
| 12 | −15.6642 | 0.6244 | | |
| 13 | ∞ | 0.5305 | 1.51633 | 64.14 |
| 14 | ∞ | 0.0152 | 1.51300 | 64.00 |
| 15 | ∞ | 0.6063 | 1.61062 | 50.49 |
| 16 | ∞ | 0.0151 | 1.51300 | 64.00 |
| 17 | ∞ | 0.6025 | 1.61062 | 50.49 |
| 18 (Image plane) | ∞ | 0 | | |

| Various data | |
|---|---|
| IH | 0.785 |
| ω | 49.819 |
| Fno | 3.902 |

Example 10

| Unit mm | | | | |
|---|---|---|---|---|
| Surface data | | | | |
| Surface no. | r | d | nd | νd |
| 1 | ∞ | 0.7091 | 1.88300 | 40.76 |
| 2 | 1.5748 | 1.2402 | | |
| 3 | ∞ | 0.7091 | 1.51633 | 64.14 |
| 4 | ∞ | 0.0709 | | |
| 5 | ∞ | 4.1075 | 1.88300 | 40.76 |
| 6 | ∞ | 0 | | |
| 7(Stop) | ∞ | 0.3344 | | |
| 8 | 4.7563 | 1.4638 | 1.75500 | 52.32 |
| 9 | −4.7563 | 0.1064 | | |
| 10 | ∞ | 1.0636 | 1.52100 | 65.13 |
| 11 | ∞ | 0.1418 | | |
| 12 | 2.6909 | 1.7969 | 1.58913 | 61.14 |
| 13 | −2.0324 | 0.5318 | 1.92286 | 18.90 |
| 14 | −12.6152 | 0.6184 | | |
| 15 | ∞ | 0.6205 | 1.88300 | 40.76 |
| 16 | ∞ | 0.0177 | 1.51300 | 64.00 |

-continued

| Unit mm | | | | |
|---|---|---|---|---|
| 17 | ∞ | 0.7091 | 1.61062 | 50.49 |
| 18 (Image plane) | ∞ | 0 | | |

| Various data | |
|---|---|
| IH | 0.775 |
| ω | 49.712 |
| Fno | 4.826 |

-continued

| Unit mm | | | | |
|---|---|---|---|---|
| 17 | ∞ | 0.7148 | 1.61062 | 50.49 |
| 18 (Image plane) | ∞ | 0 | | |

| Various data | |
|---|---|
| IH | 0.781 |
| ω | 49.8 |
| Fno | 4.679 |

Example 11

| Unit mm | | | | |
|---|---|---|---|---|
| Surface data | | | | |
| Surface no. | r | d | nd | vd |
| 1 | ∞ | 0.7151 | 1.88300 | 40.76 |
| 2 | 1.6305 | 1.2317 | | |
| 3 | ∞ | 0.7151 | 1.51633 | 64.14 |
| 4 | ∞ | 0.0715 | | |
| 5 | ∞ | 4.1421 | 1.88300 | 40.76 |
| 6 | ∞ | 0 | | |
| 7(Stop) | ∞ | 0.2647 | | |
| 8 | 5.3567 | 1.0020 | 1.75500 | 52.32 |
| 9 | −4.4586 | 0.1073 | | |
| 10 | ∞ | 1.0726 | 1.52100 | 65.13 |
| 11 | ∞ | 0.1430 | | |
| 12 | 3.4196 | 1.9581 | 1.72916 | 54.68 |
| 13 | −1.6984 | 0.5363 | 1.92286 | 18.90 |
| 14 | −15.0024 | 0.6204 | | |
| 15 | ∞ | 0.6257 | 1.88300 | 40.76 |
| 16 | ∞ | 0.0179 | 1.51300 | 64.00 |
| 17 | ∞ | 0.7151 | 1.61062 | 50.49 |
| 18 (Image plane) | ∞ | 0 | | |

| Various data | |
|---|---|
| IH | 0.781 |
| ω | 49.83 |
| Fno | 4.686 |

Example 13

| Unit mm | | | | |
|---|---|---|---|---|
| Surface data | | | | |
| Surface no. | r | d | nd | vd |
| 1 | ∞ | 0.5257 | 1.88300 | 40.76 |
| 2 | 1.3088 | 0.7804 | | |
| 3 | ∞ | 0.5257 | 1.51633 | 64.14 |
| 4 | ∞ | 0.0526 | | |
| 5 | ∞ | 3.0450 | 1.80610 | 40.92 |
| 6 | ∞ | 0 | | |
| 7(Stop) | ∞ | 0.0848 | | |
| 8 | 3.7410 | 1.1367 | 1.75500 | 52.32 |
| 9 | −3.5359 | 0.0789 | | |
| 10 | ∞ | 0.7885 | 1.52100 | 65.13 |
| 11 | ∞ | 0.1051 | | |
| 12 | 2.3989 | 1.5316 | 1.58913 | 61.14 |
| 13 | −1.2564 | 0.4164 | 1.80810 | 22.76 |
| 14 | −33.5075 | 0.6417 | | |
| 15 | ∞ | 0.4600 | 1.51633 | 64.14 |
| 16 | ∞ | 0.0131 | 1.51300 | 64.00 |
| 17 | ∞ | 0.5257 | 1.61062 | 50.49 |
| 18 (Image plane) | ∞ | 0 | | |

| Various data | |
|---|---|
| IH | 0.769 |
| ω | 47.829 |
| Fno | 4.29 |

Example 12

| Unit mm | | | | |
|---|---|---|---|---|
| Surface data | | | | |
| Surface no. | r | d | nd | vd |
| 1 | ∞ | 0.7148 | 1.88300 | 40.76 |
| 2 | 1.6360 | 1.2338 | | |
| 3 | ∞ | 0.7148 | 1.51633 | 64.14 |
| 4 | ∞ | 0.0715 | | |
| 5 | ∞ | 4.1406 | 1.88300 | 40.76 |
| 6 | ∞ | 0 | | |
| 7(Stop) | ∞ | 0.2616 | | |
| 8 | 5.7330 | 0.9374 | 1.78590 | 44.20 |
| 9 | −4.5891 | 0.1072 | | |
| 10 | ∞ | 1.0722 | 1.52100 | 65.13 |
| 11 | ∞ | 0.1430 | | |
| 12 | 3.3805 | 1.9484 | 1.72916 | 54.68 |
| 13 | −1.6935 | 0.5361 | 1.92286 | 18.90 |
| 14 | −14.9347 | 0.6272 | | |
| 15 | ∞ | 0.6255 | 1.88300 | 40.76 |
| 16 | ∞ | 0.0179 | 1.51300 | 64.00 |

Example 14

| Unit mm | | | | |
|---|---|---|---|---|
| Surface data | | | | |
| Surface no. | r | d | nd | vd |
| 1 | ∞ | 0.5392 | 1.88300 | 40.76 |
| 2 | 1.4109 | 0.7483 | | |
| 3 | ∞ | 0.5392 | 1.51633 | 64.14 |
| 4 | ∞ | 0.0539 | | |
| 5 | ∞ | 3.1230 | 1.51633 | 64.14 |
| 6 | ∞ | 0 | | |
| 7(Stop) | ∞ | 0.0809 | | |
| 8 | 4.7542 | 1.4154 | 1.77250 | 49.60 |
| 9 | −3.7982 | 0.0809 | | |
| 10 | ∞ | 0.8087 | 1.52100 | 65.13 |
| 11 | ∞ | 0.1078 | | |
| 12 | 3.4342 | 1.7847 | 1.72916 | 54.68 |
| 13 | −1.1903 | 0.5256 | 1.80810 | 22.76 |
| 14 | ∞ | 0.7540 | | |
| 15 | ∞ | 0.4718 | 1.51633 | 64.14 |
| 16 | ∞ | 0.0135 | 1.51300 | 64.00 |

-continued

Unit mm

| | | | | |
|---|---|---|---|---|
| 17 | ∞ | 0.5392 | 1.61062 | 50.49 |
| 18 (Image plane) | ∞ | 0 | | |

Various data

| | |
|---|---|
| IH | 0.789 |
| ω | 49.83 |
| Fno | 4.282 |

Example 15

Unit mm

Surface data

| Surface no. | r | d | nd | vd |
|---|---|---|---|---|
| 1 | ∞ | 0.6803 | 1.88300 | 40.76 |
| 2 | 1.5386 | 1.1825 | | |
| 3 | ∞ | 0.6803 | 1.51633 | 64.14 |
| 4 | ∞ | 0.0680 | | |
| 5 | ∞ | 3.9405 | 1.88300 | 40.76 |
| 6 | ∞ | 0 | | |
| 7(Stop) | ∞ | 0.3052 | | |
| 8 | 5.2193 | 1.3688 | 1.77250 | 49.60 |
| 9 | −4.3467 | 0.1020 | | |
| 10 | ∞ | 1.0204 | 1.52100 | 65.13 |
| 11 | ∞ | 0.1361 | | |
| 12 | 2.5755 | 1.6909 | 1.58913 | 61.14 |
| 13 | −2.0613 | 0.5201 | 1.95906 | 17.47 |
| 14 | −13.8236 | 0.6296 | | |
| 15 | ∞ | 0.5952 | 1.51633 | 64.14 |
| 16 | ∞ | 0.0170 | 1.51300 | 64.00 |
| 17 | ∞ | 0.6803 | 1.61062 | 50.49 |
| 18 (Image plane) | ∞ | 0 | | |

Various data

| | |
|---|---|
| IH | 0.881 |
| ω | 59.74 |
| Fno | 3.569 |

The values of conditional expressions (1) to (9) in example 1 to example 15 of the objective optical system are shown below.

| | Example 1 | Example 2 | Example 3 |
|---|---|---|---|
| (1) $f_F/f$ | −1.553 | −1.528 | −1.468 |
| (2) $f_R/f$ | 2.062 | 2.056 | 2.069 |
| (3) $|f_F/f_R|$ | 0.753 | 0.743 | 0.709 |
| (4) D1/f | 3.166 | 3.179 | 3.139 |
| (5) D2/f | 1.274 | 1.217 | 1.395 |
| (6) D1/D2 | 2.486 | 2.613 | 2.25 |
| (7) $f_3/f_2$ | 3.008 | 2.962 | 2.681 |
| (8) $|R_c|/f$ | 1.561 | 1.629 | 1.493 |
| (9) TW | −10.032 | −10.411 | −10 |

| | Example 4 | Example 5 | Example 6 |
|---|---|---|---|
| (1) $f_F/f$ | −1.675 | −1.675 | −1.583 |
| (2) $f_R/f$ | 2.108 | 2.108 | 2.163 |
| (3) $|f_F/f_R|$ | 0.794 | 0.794 | 0.732 |
| (4) D1/f | 2.946 | 2.946 | 3.307 |
| (5) D2/f | 1.535 | 1.535 | 1.362 |
| (6) D1/D2 | 1.92 | 1.92 | 2.428 |
| (7) $f_3/f_2$ | 2.55 | 2.55 | 2.612 |
| (8) $|R_c|/f$ | 1.639 | 1.639 | 1.649 |
| (9) TW | −7.365 | −7.59 | −9.433 |

| | Example 7 | Example 8 | Example 9 |
|---|---|---|---|
| (1) $f_F/f$ | −1.591 | −1.623 | −1.59 |
| (2) $f_R/f$ | 2.179 | 2.08 | 2.16 |
| (3) $|f_F/f_R|$ | 0.73 | 0.78 | 0.736 |
| (4) D1/f | 3.385 | 3.361 | 3.320 |
| (5) D2/f | 1.372 | 1.356 | 1.361 |
| (6) D1/D2 | 2.467 | 2.478 | 2.440 |
| (7) $f_3/f_2$ | 2.673 | 2.555 | 2.601 |
| (8) $|R_c|/f$ | 1.644 | 1.666 | 1.649 |
| (9) TW | −9.563 | −10.863 | −9.529 |

| | Example 10 | Example 11 | Example 12 |
|---|---|---|---|
| (1) $f_F/f$ | −1.783 | −1.847 | −1.853 |
| (2) $f_R/f$ | 2.457 | 2.395 | 2.382 |
| (3) $|f_F/f_R|$ | 0.726 | 0.771 | 0.778 |
| (4) D1/f | 3.96 | 3.975 | 3.976 |
| (5) D2/f | 1.4 | 1.408 | 1.415 |
| (6) D1/D2 | 2.829 | 2.822 | 2.81 |
| (7) $f_3/f_2$ | 1.996 | 1.733 | 1.705 |
| (8) $|R_c|/f$ | 2.032 | 1.698 | 1.693 |
| (9) TW | −7.277 | −8.003 | −8.17 |

| | Example 13 | Example 14 | Example 15 |
|---|---|---|---|
| (1) $f_F/f$ | −1.482 | −1.598 | −1.742 |
| (2) $f_R/f$ | 1.927 | 2.159 | 2.37 |
| (3) $|f_F/f_R|$ | 0.769 | 0.74 | 0.735 |
| (4) D1/f | 2.866 | 3.217 | 3.792 |
| (5) D2/f | 1.28 | 1.409 | 1.456 |
| (6) D1/D2 | 2.239 | 2.284 | 2.605 |
| (7) $f_3/f_2$ | 2.973 | 2.115 | 2.125 |
| (8) $|R_c|/f$ | 1.256 | 1.19 | 2.061 |
| (9) TW | −11.235 | −9.216 | −8.876 |

| | Example 1 | Example 2 | Example 3 |
|---|---|---|---|
| f | 1 | 1 | 1 |
| $f_F$ | −1.553 | −1.528 | −1.468 |
| $f_R$ | 2.062 | 2.056 | 2.069 |
| D1 | 3.166 | 3.179 | 3.139 |
| D2 | 1.274 | 1.217 | 1.395 |
| $f_2$ | 2.779 | 2.848 | 2.916 |
| $f_3$ | 8.358 | 8.438 | 7.818 |
| $R_c$ | −1.561 | −1.629 | −1.493 |

| | Example 4 | Example 5 | Example 6 |
|---|---|---|---|
| f | 1 | 1 | 1 |
| $f_F$ | −1.675 | −1.675 | −1.583 |
| $f_R$ | 2.108 | 2.108 | 2.163 |
| D1 | 2.946 | 2.946 | 3.307 |
| D2 | 1.535 | 1.535 | 1.362 |
| $f_2$ | 2.608 | 2.608 | 2.93 |
| $f_3$ | 6.652 | 6.652 | 7.655 |
| $R_c$ | −1.639 | −1.639 | −1.649 |

| | Example 7 | Example 8 | Example 9 |
|---|---|---|---|
| f | 1 | 1 | 1 |
| $f_F$ | −1.591 | −1.623 | −1.59 |
| $f_R$ | 2.179 | 2.08 | 2.16 |
| D1 | 3.385 | 3.361 | 3.320 |
| D2 | 1.372 | 1.356 | 1.361 |
| $f_2$ | 2.954 | 2.878 | 2.932 |
| $f_3$ | 7.896 | 7.355 | 7.625 |
| $R_c$ | −1.644 | −1.666 | −1.649 |

| | Example 10 | Example 11 | Example 12 |
|---|---|---|---|
| f | 1 | 1 | 1 |
| $f_F$ | −1.783 | −1.847 | −1.853 |
| $f_R$ | 2.457 | 2.395 | 2.382 |
| D1 | 3.96 | 3.975 | 3.976 |
| D2 | 1.4 | 1.408 | 1.415 |
| $f_2$ | 3.373 | 3.371 | 3.378 |

-continued

|     | | | |
| --- | --- | --- | --- |
| $f_3$ | 6.734 | 5.841 | 5.758 |
| $R_c$ | −2.032 | −1.698 | −1.693 |

|     | Example 13 | Example 14 | Example 15 |
| --- | --- | --- | --- |
| f   | 1 | 1 | 1 |
| $f_F$ | −1.482 | −1.598 | −1.742 |
| $f_R$ | 1.927 | 2.159 | 2.37 |
| D1  | 2.866 | 3.217 | 3.792 |
| D2  | 1.28 | 1.409 | 1.456 |
| $f_2$ | 2.581 | 2.946 | 3.274 |
| $f_3$ | 7.673 | 6.229 | 6.957 |
| $R_c$ | −1.256 | −1.19 | −2.061 |

Figure 22:
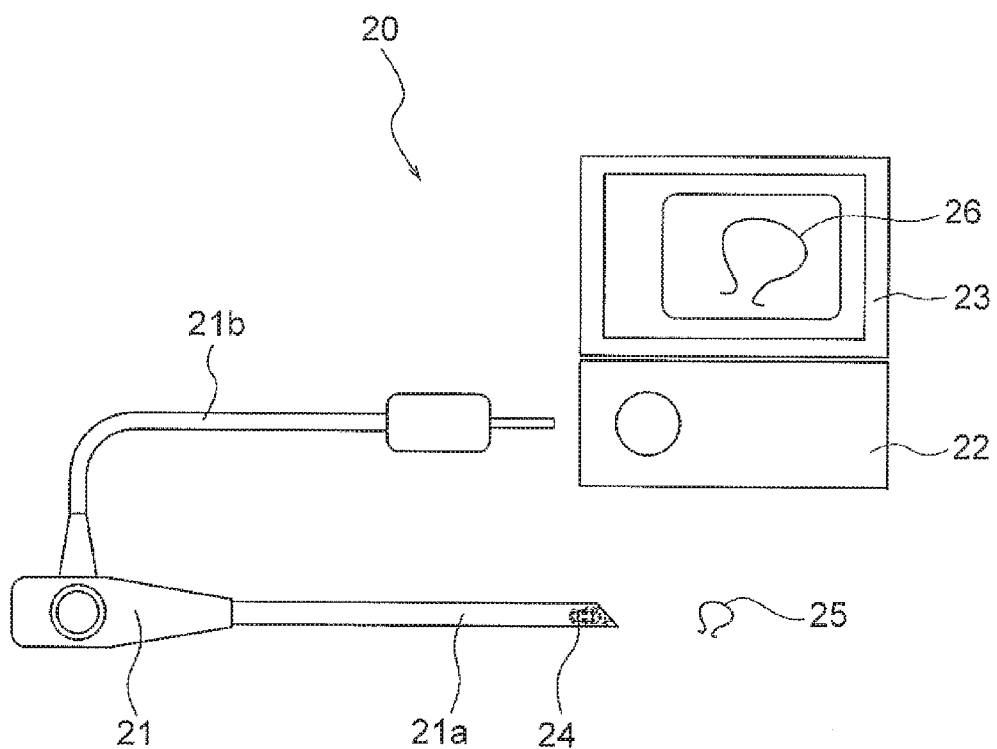
FIG. 22 is a diagram showing an arrangement of an endoscope apparatus.

FIG. 22 is an example of an arrangement of an endoscope apparatus in which the oblique-viewing objective optical system of the present embodiment is used. An endoscope apparatus 20 includes an endoscope for oblique viewing 21 (hereinafter, referred to as the 'endoscope 21'), a video processor 22, and a monitor 23. The endoscope 21 includes an inserting portion 21a and a signal cable 21b. An oblique-viewing objective optical system 24 is disposed at a front end of the inserting portion 21a. In this case, the oblique-viewing objective optical system 24 is an oblique-viewing objective optical system for front-view observation. Any one of the oblique-viewing objective optical systems according to the examples 1 to 15 is to be used as the oblique-viewing objective optical system 24.

Moreover, although it is not shown in the diagram, an illumination optical system which illuminates an object 25 is disposed near the oblique-viewing objective optical system 24. The illumination optical system includes a light source, an illumination optical element, and an optical fiber bundle. As the light source, light emitting elements such as a light-emitting diode (LED: Light Emitting Diode) and a laser diode (LD: Laser Diode) are available. As the illumination optical element, a lens element is available. A lens element has a function of diffusing or focusing illumination light. The optical fiber bundle transmits the illumination light to the endoscope 21.

Moreover, the endoscope 21 is connected to the video processor 22 via the signal cable 21b. An image of the object 25 formed by the oblique-viewing objective optical system 24 is captured by the image pickup element. The image of the object 25 that has been captured is converted to a video signal by an electric-circuit system built-in in the video processor 22. Based on the video signal, a video picture 26 is displayed on the monitor 23.

An electric circuit system which drives the light source such as an LED is provided to an interior of the video processor 22.

Moreover, by providing a light-emitting element such as an LED and LD inside the endoscope 21, there is no need to provide a light source outside the endoscope 21. Furthermore, by providing these light-emitting elements to a front-end portion of the endoscope 21, there is no need to provide the optical fiber bundle that transmits the illumination light.

Furthermore, a lamp such as a xenon lamp or a halogen lamp may be used as the light source. Moreover, in the endoscope apparatus 20, a light-source unit having a built-in light source may be integrated with the video processor 22. However, the light-source unit may be arranged separately from the video processor 22. In this case, the light-source unit and the video processor 22 are to be connected separately to the endoscope 21.

As described heretofore, according to the oblique-viewing objective optical system of the present invention, it is possible to provide an oblique-viewing objective optical system with a high performance and small size, optimum for an image pickup element in which increasing number of pixels and small-sizing have been made, while improving assemblability and an ability to install on a front-end portion of endoscope. Furthermore, by using the oblique-viewing objective optical system of the present invention, it is possible to achieve a high-quality image, and to provide an endoscope for oblique viewing having a front-end portion with a thinned diameter.

Various embodiments of the present invention have been described heretofore. However, the present invention is not limited only to the embodiments described above, and embodiments in which arrangements of these embodiments have been combined appropriately without departing from the scope of the invention are also within the scope of the present invention.

APPENDED MODE

The present invention also includes the following inventions which are conceived form abovementioned embodiments and examples.

Appended Mode 1

An oblique-viewing objective optical system, comprising in order from an object side:
a front-side lens group which includes a negative lens;
an optical path converting element;
an aperture stop; and
a rear-side lens group having a positive refractive power, wherein
the rear-side lens group includes a positive lens and a cemented lens having a positive refractive power, and
the cemented lens includes in order from the object side, a positive lens and a negative lens, and
the following conditional expressions (1), (2), and (3) are satisfied:

$$-2.0 < f_F/f < -1.3 \qquad (1),$$

$$1.7 < f_R/f < 2.7 \qquad (2), \text{ and}$$

$$0.63 < |f_F/f_R| < 0.88 \qquad (3),$$

where,
$f_F$ denotes a focal length of the front-side lens group,
$f_R$ denotes a focal length of the rear-side lens group, and
f denotes a focal length of the overall oblique-viewing objective optical system.

Appended Mode 2

The oblique-viewing objective optical system according to Appended Mode 1, wherein,
the following conditional expressions (4) and (5) are satisfied:

$$2.4 < D1/f < 4.4 \qquad (4), \text{ and}$$

$$1.1 < D2/f < 1.7 \qquad (5),$$

where,
D1 denotes an air-conversion length from an image-side surface of the negative lens in the front-side lens group up to the aperture stop,
D2 denotes an air-conversion length from an image-side surface of the rearmost lens in the rear-side lens group up to the image plane, and
f denotes the focal length of the overall oblique-viewing objective optical system.

Appended Mode 3

The oblique-viewing objective optical system according to Appended Mode 1 or Appended Mode 2, wherein,
the following conditional expression (6) is satisfied:

$$1.7 < D1/D2 < 3.1 \quad (6),$$

where,
D1 denotes the air-conversion length from the image-side surface of the negative lens in the front-side lens group up to the aperture stop, and
D2 denotes the air-conversion length from an image-side surface of the rearmost lens in the rear-side lens group up to image plane.

Appended Mode 4

The oblique-viewing objective optical system according to any one of Appended Modes 1 to 3, wherein
the following conditional expression (7) is satisfied:

$$1.5 < f_3/f_2 < 3.1 \quad (7),$$

where,
$f_2$ denotes a focal length of a positive lens in the rear-side lens group, and
$f_3$ denotes a focal length of the cemented lens in the rear-side lens group.

Appended Mode 5

The oblique-viewing objective optical system according to any one of Appended Modes 1 to 4, wherein
the following conditional expression (8) is satisfied:

$$1.1 < |R_c|/f < 2.1 \quad (8),$$

where,
$R_c$ denotes a radius of curvature of a cemented surface of the cemented lens in the rear-side lens group, and
f denotes the focal length of the overall oblique-viewing objective optical system.

Appended Mode 6

The oblique-viewing objective optical system according to any one of Appended Modes 1 to 5, wherein
the following conditional expression (9) is satisfied:

$$-17° < TW < 0° \quad (9),$$

where,
TW denotes an angle of incidence of a light ray on the image plane when the image height is the maximum.

Appended Mode 7

An endoscope for oblique viewing, comprising:
an oblique-viewing objective optical system according to any one of Appended Modes 1 to 6.

According to the present invention, it is possible to realize an oblique-viewing objective optical system having a high performance and small size that can be assembled and installed on a front-end portion of an endoscope with high accuracy and easily. Moreover, it is possible to provide an endoscope for oblique viewing which is capable of obtaining a high-quality image, and has a front-end portion with a thinned diameter.

As described heretofore, the present invention is useful for an oblique-viewing objective optical system having a high performance and small size that can be assembled and installed on a front-end portion of an endoscope with high accuracy and easily. Moreover, the present invention is useful for an endoscope for oblique viewing which is capable of obtaining a high-quality image, and has a front-end portion with a thinned diameter.

What is claimed is:
1. An oblique-viewing objective optical system, comprising in order from an object side:
a front-side lens group which includes a negative lens;
an optical path converting element;
an aperture stop; and
a rear-side lens group having a positive refractive power,
wherein:
the rear-side lens group includes a positive lens and a cemented lens having a positive refractive power,
the cemented lens includes in order from the object side, a positive lens and a negative lens, and
the following conditional expressions (1), (2), (3), (4), and (5) are satisfied:

$$-2.0 < f_F/f < -1.3 \quad (1),$$

$$1.7 < f_R/f < 2.7 \quad (2),$$

$$0.63 < |f_F/f_R| < 0.88 \quad (3),$$

$$2.4 < D1/f < 4.4 \quad (4), \text{ and}$$

$$1.1 < D2/f < 1.7 \quad (5),$$

where:
$f_F$ denotes a focal length of the front-side lens group,
$f_R$ denotes a focal length of the rear-side lens group,
f denotes a focal length of the overall oblique-viewing objective optical system,
D1 denotes an air-conversion length from an image-side surface of the negative lens in the front-side lens group up to the aperture stop, and
D2 denotes an air-conversion length from an image-side surface of the negative lens of the cemented lens in the rear-side lens group up to an image plane.
2. An endoscope for oblique viewing, comprising:
an oblique-viewing objective optical system according to claim 1.

* * * * *